(12) United States Patent
Van de Lavoir et al.

(10) Patent No.: US 7,145,057 B2
(45) Date of Patent: Dec. 5, 2006

(54) CHIMERIC BIRD FROM EMBRYONIC STEM CELLS

(75) Inventors: Marie-Cecile Van de Lavoir, San Francisco, CA (US); Robert J. Etches, San Mateo, CA (US); Babette Heyer, Menlo Park, CA (US); Jennifer Diamond, Millbrae, CA (US); Christine Mather, Millbrae, CA (US); Kathleen Beemer, Pacifica, CA (US); Heather Myers, Danville, CA (US)

(73) Assignee: Origen Therapeutics, Inc., Burlingame, CA (US)

( * ) Notice: Subject to any disclaimer, the term of this patent is extended or adjusted under 35 U.S.C. 154(b) by 0 days.

(21) Appl. No.: 10/067,148

(22) Filed: Feb. 1, 2002

(65) Prior Publication Data

US 2003/0170888 A1 Sep. 11, 2003

(51) Int. Cl.
*A01K 67/00* (2006.01)
*C12N 15/00* (2006.01)
*C12N 5/00* (2006.01)
*C12N 5/06* (2006.01)
*C12N 15/63* (2006.01)

(52) U.S. Cl. .............................. 800/19; 800/8; 800/21; 800/25; 435/320.1; 435/325; 435/349; 435/455

(58) Field of Classification Search .................... 800/8, 800/19, 21, 25; 435/320.1, 325, 349, 455
See application file for complete search history.

(56) References Cited

U.S. PATENT DOCUMENTS

| | | | |
|---|---|---|---|
| 5,162,215 A | 11/1992 | Bosselman et al. | |
| 5,340,740 A | 8/1994 | Petitte et al. | 435/340.2 |
| 5,656,479 A | 8/1997 | Petitte et al. | 435/349 |
| 5,830,510 A * | 11/1998 | Petitte et al. | 424/582 |
| 5,897,998 A | 4/1999 | Speksnijder et al. | |
| 6,114,168 A | 9/2000 | Samarut et al. | 435/405 |
| 6,156,569 A | 12/2000 | Ponce de Leon et al. | |
| 6,287,863 B1 | 9/2001 | Hodgson | 435/455 |
| 6,333,192 B1 | 12/2001 | Petitte et al. | 435/349 |
| 6,515,199 B1 | 2/2003 | Petitte et al. | |

FOREIGN PATENT DOCUMENTS

| | | |
|---|---|---|
| WO | WO 90/01541 | 2/1990 |
| WO | WO 93/23528 | 11/1993 |
| WO | WO 96/12793 | 5/1996 |
| WO | WO 00/11892 | 1/2000 |
| WO | WO 00/75300 | 6/2000 |
| WO | WO 00/47717 A1 | 8/2000 |
| WO | WO 02/12437 A2 | 2/2002 |
| WO | WO 03/043415 A1 | 11/2002 |
| WO | WO 03/076601 A1 | 3/2003 |

OTHER PUBLICATIONS van de Lavoir et al, High-grade transgenic somatic chimeras from chicken embryonic stem cells. Mech. Dev. 123(1):31-41, 2006.*
"Avian transgenesis: progress towards the promise," Ivarie, Robert, Trends in Biotechnol. vol. 21, No. 1 Jan. 2003.
"The Avian Germline and Strategies for the Production of Transgenic Chickens," Petitte, James N., J. of Poultry Science, 39: 205-228, Jul. 2002.
"Transgenic Chickens: Past, Present and Future," Zajchowski, L.D. et al., Poultry and Avian Biology Reviews 11(2):63-80 2000.
"Chicken Embryonic Stem Cells and Transgenic Strategies," B. Pain et al., Cells Tissues Organs 1999; 165:212-219.
"Long-term in vitro culture and characterisation of avian embryonic stem cells with multiple mophogenetic potentialities," Pain, B. et al., Development 122 2339-2348, 1996).
"Transgenic chickens—methods and potential applications," Sang, Helen, Trends in Biotechnol. 12:415-420 (1994).
"Transgenesis in Chickens," Perry, Margaret M. et al., Transgenic Research 2, 125-133 (1993).
"Novel approaches to studies of avian endocrinology using transgenic chickens produced via chimeric intermediates," Etches, R.J. et al., In Avian Endocrinology, Edited by P.J. Sharp, pp. 381-396, 1993 J. of Endocrinology, Bristol, UK.
Etches, R.J., "A Genetic Approach to Physiology," Chapter 1, pp. 1-13 in "Manipulation of the Avian Genome" edited by R.J. Etches and A.M. Verrinder Gibbins (1993), CRC Press, Boca Raton.
"Production of somatic and germline chimeras in the chicken by transfer of early blastodermal cells," Petitte, J.N. et al., Development 108, 185-189 (1990).
"Production of transgenic birds," Shuman, R.M., Experientia 47, 897-905 (1991).
"Efficient Transfer of Chicken Blastodermal Cells and Their Incorporation Into Recipient Embryos to Produce Chimeric Chicks," Gibbins, A.M Verrinder et al., Proceedings of the 4th World Congress on Genetics Applied to Livestock Production XVI, 119-122, Edinburgh: Jul. 23-27, 1990.

(Continued)

*Primary Examiner*—Sumesh Kaushal
(74) *Attorney, Agent, or Firm*—Orrick, Herrington & Sutcliffe LLP

(57) ABSTRACT

Sustained cultures of avian embryonic stem cells are provided. Injection of avian embryonic stem cells into recipient embryos yields chimeras with a significant contribution from the embryonic stem cell phenotype. Transgene encoding exogenous proteins are stably integrated in the embryonic stem cells and are present in the somatic tissue of the resulting chimeras. The transgenes may encode exogenous proteins expressed in endodermal, ectodermal, mesodermal, or extra embryonic tissue. Breeding the resulting chimera yields transgenic birds whose genome is comprised of exogenous DNA.

9 Claims, 23 Drawing Sheets

OTHER PUBLICATIONS

"Production of chimeric chicks by blastodermal stem cell transfer and the prospects for gene manipulation," Etches, R.J. et al., In Avian Incubation and Embryology, Edited by S. Tullett p. 305-309 1990, 22nd British Poultry Science Symposium, British Poultry Science, Edinburgh.

"Poultry Genetics by the Year 2000," Etches, R.J. et al., Department of Animal and Poultry Science, University of Guelph, published 1990.

Acloque, Hervc et al., "Identification of a new gene family specifically expressed in chicken embryonic stem cells and early embryo," Mechanisms of Development 103 (2001) 79-91.

Acloque Herve et al., "Indentification of a new gene family specifically expressed in chicken embryonic stem cells and early embryo," Mechanisms of Development 103 (2001) 79-91.

* cited by examiner

Fig 2
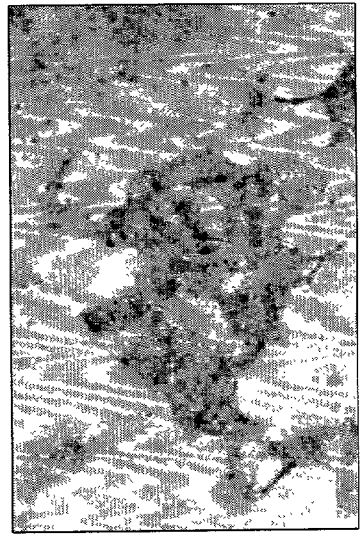
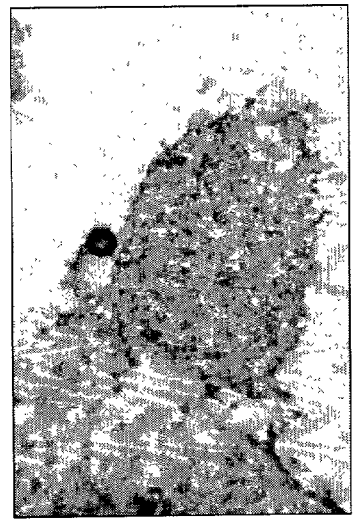
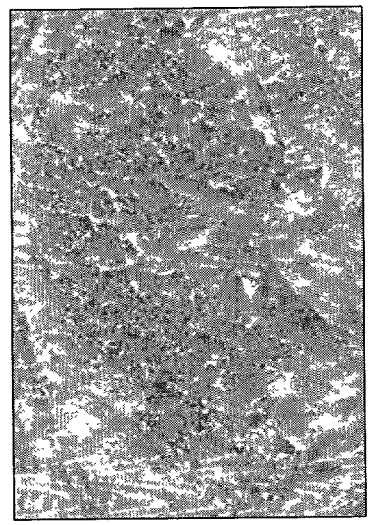
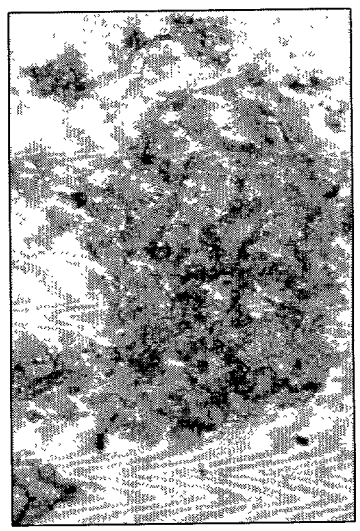

pCxGFP/Puro

ES cells expressing EGFP

Same field under phase

A. Ov7.5MAbdns

B. Ov15MAbdns

Fig 13

Fig 15
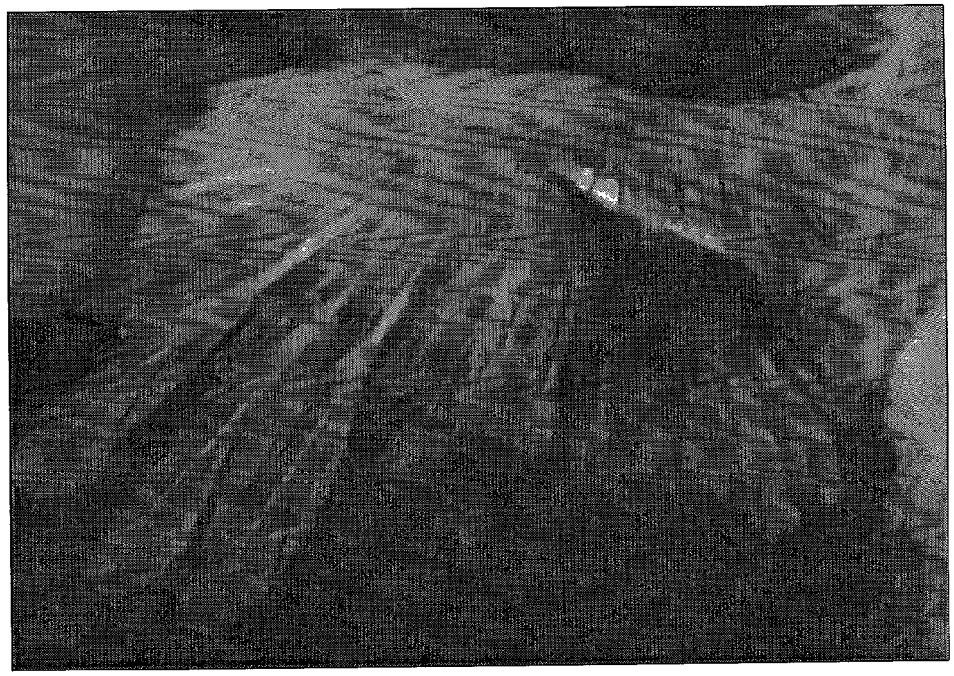
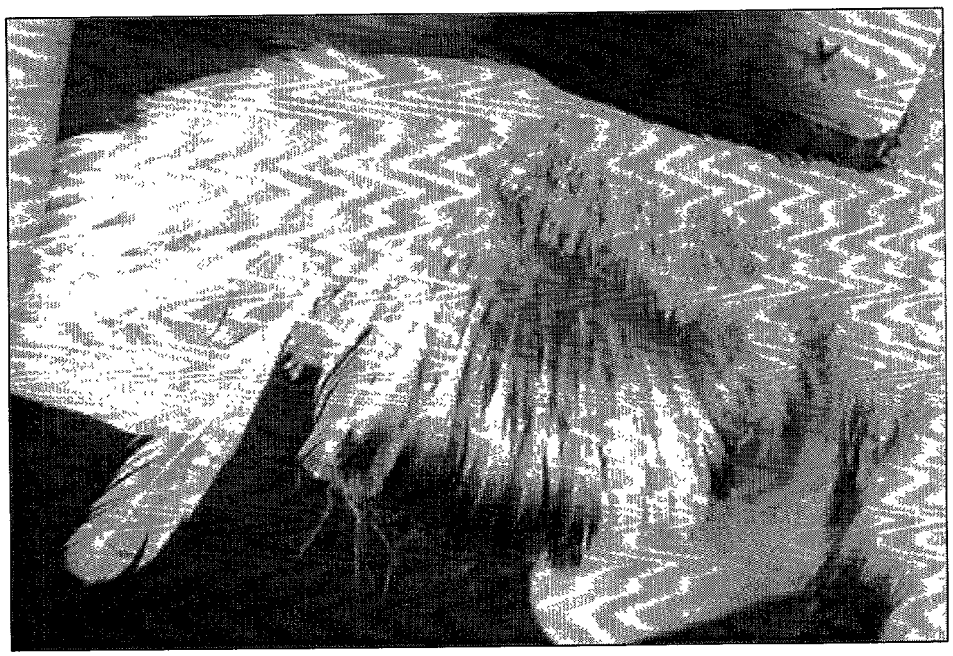

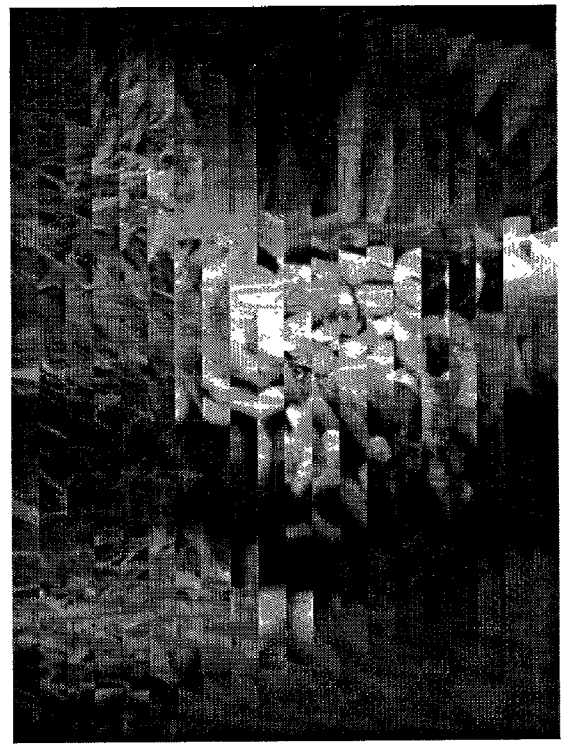
Fig 16

Fig 17

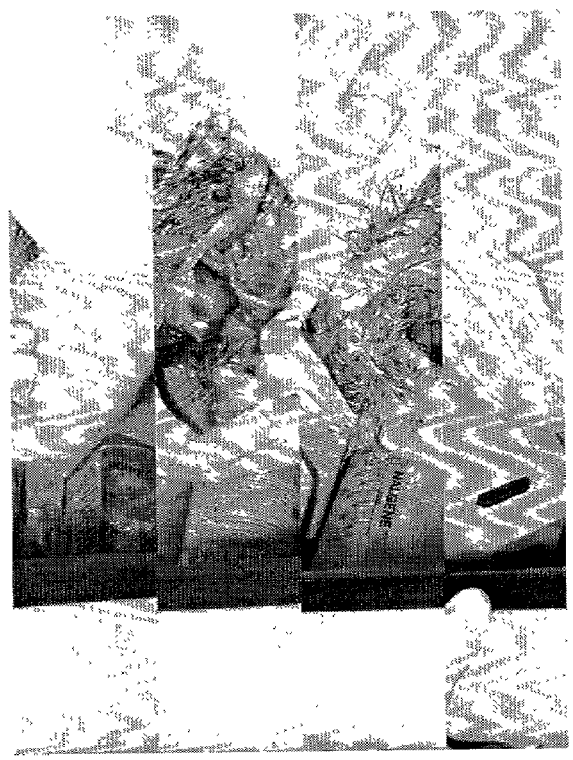
Fig 18

Flow cytometric analysis of green fluorescence from Dispersed brain cells from juvenile chimeras. Cell count on y-axis, fluorescence intensity on x-axis.

1 - chimeras made with untransfected cES cells
2 - chimeras made with cES cells stably transfected with GFP

```
                              SEQUENCE LISTING

<160> NUMBER OF SEQ ID NOS: 10

<210> SEQ ID NO 1
<211> LENGTH: 24
<212> TYPE: DNA
<213> ORGANISM: Artificial sequence
<220> FEATURE:
<223> OTHER INFORMATION: VH6-1 forward primer

<400> SEQUENCE: 1
agtgtcaggg agatgccgta ttca                                              24

<210> SEQ ID NO 2
<211> LENGTH: 23
<212> TYPE: DNA
<213> ORGANISM: Artificial sequence
<220> FEATURE:
<223> OTHER INFORMATION: VH6-1 reverse primer

<400> SEQUENCE: 2
acttcccctc actgtgtctc ttg                                               23

<210> SEQ ID NO 3
<211> LENGTH: 21
<212> TYPE: DNA
<213> ORGANISM: Artificial sequence
<220> FEATURE:
<223> OTHER INFORMATION: D1-26 forward primer

<400> SEQUENCE: 3
gggcgcctgg gtggattctg a                                                 21

<210> SEQ ID NO 4
<211> LENGTH: 24
<212> TYPE: DNA
<213> ORGANISM: Artificial sequence
<220> FEATURE:
<223> OTHER INFORMATION: D1-26 reverse primer

<400> SEQUENCE: 4
gtggccccta aacctgagtc tgct                                              24

<210> SEQ ID NO 5
<211> LENGTH: 21
<212> TYPE: DNA
<213> ORGANISM: Artificial sequence
<220> FEATURE:
<223> OTHER INFORMATION: D1-20 forward primer

<400> SEQUENCE: 5
cccgagcacc gtccccattg a                                                 21

<210> SEQ ID NO 6
<211> LENGTH: 24
<212> TYPE: DNA
<213> ORGANISM: Artificial sequence
```

```
<220> FEATURE:
<223> OTHER INFORMATION: D1-20 reverse primer

<400> SEQUENCE: 6
gtgccggtga tccctgtctt tctg                                              24

<210> SEQ ID NO 7
<211> LENGTH: 22
<212> TYPE: DNA
<213> ORGANISM: Artificial sequence
<220> FEATURE:
<223> OTHER INFORMATION: C-mu forward primer

<400> SEQUENCE: 7
gcgggagtcg gccaccatca cg                                                22

<210> SEQ ID NO 8
<211> LENGTH: 22
<212> TYPE: DNA
<213> ORGANISM: Artificial sequence
<220> FEATURE:
<223> OTHER INFORMATION: C-mu reverse primer

<400> SEQUENCE: 8
agcacagccg ccgccccagt ag                                                22

<210> SEQ ID NO 9
<211> LENGTH: 20
<212> TYPE: DNA
<213> ORGANISM: Artificial sequence
<220> FEATURE:
<223> OTHER INFORMATION: C-delta forward primer

<400> SEQUENCE: 9
tggggagagg agagcacagt                                                   20

<210> SEQ ID NO 10
<211> LENGTH: 19
<212> TYPE: DNA
<213> ORGANISM: Artificial sequence
<220> FEATURE:
<223> OTHER INFORMATION: C-delta reverse primer

<400> SEQUENCE: 10
ggcgggcgta ggggtcagc                                                    19
```

CHIMERIC BIRD FROM EMBRYONIC STEM CELLS

This invention was made in part from government support under Grant No. R44 HD 39583 National Institute of Health (NIH) of the United States. The U.S. Government may have certain rights in this invention.

FIELD OF THE INVENTION

This invention relates to the field of transgenic and chimeric animals, and specifically to long-term cultures of avian embryonic stem cells. The embryonic stem cells are sustained in long-term cultures and produce chimeras when injected into recipient embryos. The embryonic stem cells may contain engineered genetic constructs and may be used to introduce genetic modification into birds, including by the insertion of transgenes encoding exogenous proteins. Birds hatched from recipient embryos broadly express the transgene-derived exogenous protein in their somatic and germ-line tissue.

BACKGROUND OF THE INVENTION

The production of genetically engineered animals offers the potential for tremendous advances in the production of valuable animals having defined genetic characteristics and for the production of valuable pharmaceutical products from the cells of such animals. However, the production of genetically modified animals involves significant technical hurdles that have only been overcome for a few species. The ability to incorporate genetic modifications into the permanent DNA of a species requires several distinct technologies that must be developed for each genetically engineered species. One approach to alter the genetic and physical characteristics of an animal using embryonic stem cells that can contribute to the phenotype of an animal when injected into an embryonic form of the animal. Embryonic stem cells have the ability to contribute to the tissue of a chimeric animal born from the recipient embryo and to contribute to the genome of a transgenic organism created by breeding chimeras.

Significant expenditure of time and resources has been committed to the study and development of embryonic stem cell lines and culture techniques that permit such cells to be maintained in culture, particularly where known genetic engineering techniques can be applied to modify the genome of the embryonic stem cells. Although significant expenditures have been made, the ability to sustain the pluripotency of embryonic stem cells in culture has been achieved for only a few species, notably mice. For other species, the promise of genetic engineering has been frustrated by the lack of sustainable long-term embryonic stem cell cultures.

If cultures of embryonic stem cells were readily available, a broad application of new technologies would be available. Because embryonic stem cells contribute to the permanent DNA of an animal, the physiological characteristics of the animal from which an embryonic stem cell was derived can be transferred to a recipient embryo by incorporating these cells into the recipient animal in an embryonic state. This offers two principal advantages: phenotype of animal from which embryonic stem cells are derived can be selectively transferred to a recipient embryo. Second, when the embryonic stem cell cultures are particularly stable in, the cells can be modified genetically to introduce genetic modifications into a recipient embryo in which the embryonic stem cells are introduced.

In certain cases, the embryonic stem cells can be engineered with a transgene that encodes an exogenous protein. Thus, one particularly attractive field of research and attractive area for commercial development is genetically engineered animals that express exogenous proteins in their tissues. The ability to produce exogenous proteins in cells of an animal is a particularly valuable capability when tissue specific expression is obtained.

Assuming that the embryonic stem cell culture is sufficiently stable to allow a transgene to become integrated into the genome of the embryonic stem cell, the transgene encoding the protein can be passed to a new chimeric or transgenic organism by several different techniques depending on the specific construct used as the transgene. Whole genomes can be transferred by cell hybridization, intact chromosomes by microcells, subchromosomal segments by chromosome mediated gene transfer, and DNA fragments in the kilobase range by DNA mediated gene transfer (Klobutcher, L. A. and F. H. Ruddle, Annu. Rev. Biochem., 50: 533–554, 1981). Intact chromosomes may be transferred to an embryonic stem cell by microcell-mediated chromosome transfer (MMCT) (Fournier, R. E. and F. H. Ruddle, Proc. Natl. Acad. Sci. U.S.A., 74: 319–323, 1977).

As noted above, the performance of genetic modifications in embryonic stem cells to produce transgenic animals has been demonstrated in only a very few species. For mice, the separate use of homologous recombination followed by chromosome transfer to embryonic stem (ES) cells for the production of chimeric and transgenic offspring is well known. Powerful techniques of site-specific homologous recombination or gene targeting have been developed (see Thomas, K. R. and M. R. Capecchi, Cell 51: 503–512, 1987; review by Waldman, A. S., Crit. Rev. Oncol. Hematol. 12: 49–64, 1992). Insertion of cloned DNA (Jakobovits, A., Curr. Biol. 4: 761–763, 1994), and manipulation and selection of chromosome fragments by the Cre-loxP system techniques (see Smith, A. J. et al., Nat. Genet. 9: 376–385, 1995; Ramirez-Solis, R. et al., Nature 378: 720–724, 1995; U.S. Pat. Nos. 4,959,317; 6,130,364; 6,091,001; 5,985,614) are available for the manipulation and transfer of genes into murine ES cells to produce stable genetic chimeras. Many such techniques that have proved useful in mammalian systems would be available to be applied to non-mammalian embryonic stem cells if the necessary cultures were available.

Embryonic stem cell lines suitable for use in transgenesis must be stable and maintain pluripotency when the ES cell is transfected with a genetic construct, when the genetic construct is expressed in the ES cell to allow selection of successfully transformed cells, and during the injection into recipient embryos and the formation of resulting chimeras. Moreover, the somatic tissue of the chimera must exhibit the genetic modifications derived from the embryonic stem cells, and the genetic modification must be identified in the tissue of the chimeric animal. Ideally, the embryonic stem cell could be modified to contain a transgene that would not only be incorporated into the somatic tissue of a chimeric animal, but could be effectively expressed in a wide variety of tissues in the animal, specifically individual tissue types in which the transgene is designed to be expressed. For example, transgenes encoding DNA derived from the lymphoid elements of the immune system might be targeted to be expressed in B lymphocytes of a chimeric or transgenic animal. In such circumstances, the embryonic stem cell culture must allow transformation of the genome of the embryonic stem cell with a transgene containing DNA encoding an exogenous protein, and the embryonic stem cell must contribute significantly to the genome of the resulting animal.

Avian biological systems offer many advantages including efficient farm cultivation, rapid growth, and economical production. Globally, chickens and turkeys are a major source of protein in the human diet. Further, the avian egg offers an ideal biological design, both for massive synthesis of a few proteins and ease of isolation of protein product. However, application of the full range of mammalian transgenic techniques to avian species has been unsuccessful. Most notably, the transmission to a mature, living animal of a genetic modification introduced into an avian embryonic stem cell has not been demonstrated.

To conduct the types of transgenesis in avians that has been conducted in mice requires the development of avian embryonic stem cells, which can exist in culture and maintain their pluripotential capability, i.e. express an embryonic stem cell phenotype, for an extended period of time. In many cases, the techniques necessary to introduce genetic modifications into embryonic stem cells, the screening of modified embryonic stem cells to select specific cell modifications in which the genetic constructs have been introduced, and the ability to manipulate the ES cells for injection into embryos to produce transgenic chickens, requires at least several weeks for all of the steps to be performed. In order for the embryonic stem cells to be useful in transgenesis, the pluripotential state must be maintained for the entire time period up until injection into an embryo and the ES cell must be incorporated into a recipient embryo to a substantial degree to be detected in a resulting chimeric animal.

Unless the ES cell culture conditions are ideal, embryonic stem cells begin to differentiate in a short period of time and lose the ability to contribute to the somatic tissue of a chimeric organism derived from an embryo in which the cells are injected. Thus, when differentiation occurs, cells in culture are no longer useful as pluripotential cells and also cannot be used for transgenesis. Using current avian ES cell culture techniques, the short time periods during which ES cells maintain pluripotency in culture limits their use in creating chimeras and prevents the ability to create desirable chimeric or transgenic avians, specifically those expressing exogenous proteins.

SUMMARY OF INVENTION

The present invention is long term avian ES cell cultures and techniques to produce chimeric and transgenic birds derived from prolonged embryonic stem cell cultures. In some embodiments, these pluripotent cells can be transfected with genetic constructs to modify the DNA of the ES cell, specifically to introduce a transgene encoding an exogenous protein. When combined with a host avian embryo by known procedures, those modified ES cells produce chimeric birds that incorporate the transgene into the somatic tissue of the resulting animals. These chimeric or transgenic birds exhibit an ES-cell derived phenotype and can express a selected foreign protein in a broad expression pattern. This invention includes compositions comprising long-term cultures of chicken embryonic stem cells that can be genetically modified by gene targeting, that can accept large amounts of foreign DNA, and that contribute to the somatic tissues and the germline of recipient embryos.

DESCRIPTION OF THE FIGURES

FIG. 2 shows in vitro properties of chicken ES cells, specifically the reaction with the antibodies SSEA-1 and EMA-1, and expression of alkaline phosphatase.

FIGS. 10A and 1-B: (A) A diagrammatic representation of a transgene designated Ov7.5MAbdns (upper panel); (B) A diagrammatic representation of a transgene designated Ov15Mabdns (lower panel).

FIG. 13 is a photograph of a chimeric chicken made with cES cells transfected with CX/GFP/Puro under fluorescent light (left panel) and white light (right panel). The green fluorescence in the eyes and beak show that the ES cells contributed to these tissues.

FIG. 15 is a photograph of a chimeric chicken made with cES cells transfected with CX/GFP/Puro under fluorescent light (right panel) and white light (left panel). Green fluorescence in the bones and in cells in the feather pulp of the emerging primary wing feathers indicates that the ES cells contributed to these tissues.

FIG. 16 is a photograph of a chimeric chicken made with cES cells transfected with CX/GFP/Puro under fluorescent light (left panel) and white light (right panel). The green fluorescence in the intestinal tissue and in breast muscle show that the ES cells contributed to these tissues.

FIG. 17 is a photograph of a chimeric chicken made with cES cells transfected with CX/GFP/Puro under fluorescent light (left panel) and white light (right panel). The green fluorescence in the leg muscles show that the ES cells contributed to these tissues.

FIG. 18 is a photograph of a chimeric chicken made with cES cells transfected with CX/GFP/Puro under fluorescent light (left panel) and white light (right panel). The green fluorescence in the pancreas show that the ES cells contributed to this tissue.

DETAILED DESCRIPTION OF INVENTION

Stable, long-term cultures of ES cells that yield genetically engineered chickens are necessary for several applications in avian transgenics, including to produce proteins for the pharmaceutical industry, to produce chickens that deposit human antibodies in their eggs, and to make site-specific changes to the avian genome for any number of other potential applications. The development of chimeric or transgenic avians requires that chicken embryonic stem (cES) cell lines be created that contribute to somatic tissues when injected into a recipient embryo. Specifically, the embryonic stem cell cultures are sustained for an extended length of time during which desirable phenotypes in chimeric animals resulting from the injection of embryonic stem cells can be identified, and during which chimeric modifications can be made to the genome of the embryonic stem cell to introduce exogenous DNA into a chimeric offspring. In preferred embodiments, avian embryonic stem cell cultures are maintained for an extended period of time and can be engineered to contain transgene derived DNA for the advantageous production of chimeras in which the transgene derived DNA is present in the somatic and germline tissue of the chimera. In particularly preferred embodiments, exogenous proteins encoded by the transgene are expressed in a wide range of tissue types, or in specific tissue types according to the protein encoded by the transgene.

Figure 1:
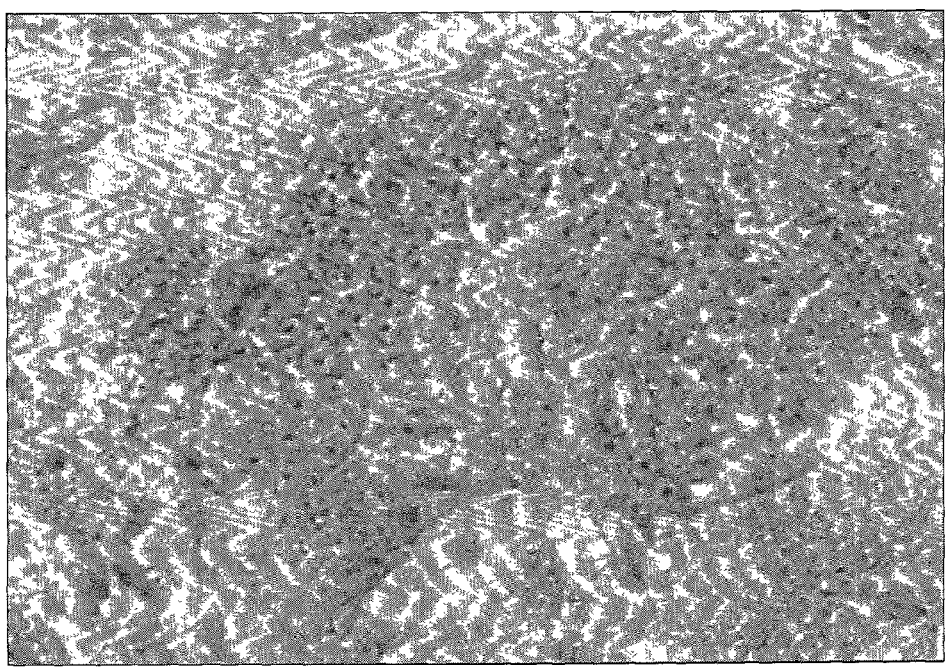
FIG. 1 shows the characteristic morphology of chicken ES cells where the small cells grow in a single layer with little cytoplasm and a prominent nucleolus.

Pursuant to this invention, chicken ES cell lines are derived from stage X embryos that have a large nucleus and contain a prominent nucleolus (FIG. 1). These cells are confirmed to be chicken embryonic stem (cES) cells by morphology after long-term culturing and to yield chimeras when injected into recipient embryos. Moreover, the ES cells enable a high degree of contribution to somatic tissues as determined by extensive feather chimerism. Still further, these embryonic stem cells are demonstrated to be transfected with transgenes carrying DNA encoding and exogenous protein. The ES cells stably integrate the transgene and express the transgene to enable selection of transformed cells. These transformed cells are capable of forming chimeras wherein an exogenous protein encoded by the transgene is present in the germline and somatic tissue of the chimera, and that cells derived from the chimera express the exogenous protein encoded by the transgene. Embryonic stem cell progeny are derivatives of ES cells that differentiate into non-ES cell phenotypes after introduction of the ES cells into recipient embryos and the formation of a chimera. A transgenic chicken is the progeny of a chimera which has been produced from chicken ES cells carrying a transgene which is stably integrated into the genome when cells derived from the transgenic ES cells have incorporated into the germline.

Expression of the transgene in somatic tissue is demonstrated in extraembryonic and somatic tissues including the allantois, endoderm, mesoderm, and ectoderm of the transgenic animal and is broadly expressed in all tissues and organ types. In a preferred embodiment, the CX promoter is used to facilitate the broad expression of GFP in somatic and germline tissues of a transgenic chicken. Analysis of the hemopoetic lineage of transgenic animals demonstrates expression in the of B lymphocytes of the immune system cells of an exogenous protein encoded by the transgene described herein using the long-term embryonic stem cells of the present invention.

EXAMPLE 1

Derivation of Chicken Embryonic Stem Cells (cES Cells)

Chicken ES cells were derived from one of two crosses: Barred Rock X Barred Rock or Barred Rock X Rhode Island Red. These breeds were selected to obtain a feather marker when testing the developmental potential of cES cells. The cES cells are injected into White Leghorn embryos, which are homozygous dominant at the dominant, white locus. Chimeric chickens resulting from injection of these ES cells display black feathers from the cES cells and white feathers from the recipient embryo.

Initial establishment of the cES cell culture was initiated according to the protocol developed by J. Petitte, see U.S. Pat. No. 5,565,479, which is specifically incorporated herein by reference. At stage X, the embryo is a small round disk, consisting of approximately 40,000–60,000 cells, situated on the surface of the yolk. To retrieve the embryo a paper ring is put on the yolk membrane, exposing the embryo in the middle. The yolk membrane is cut around the ring, which is then lifted off the yolk. The embryo, attached to the ventral side of the ring, is placed under the microscope and the area pellucida isolated from the area opaca using a fine loop.

TABLE 1 cES cell lines derived on either STO feeder cells or a polyester insert in CES-80 medium. The cultures were initiated from both single and pooled embryos.

| Cell line | Donor embryo | Substrate used to derive cES cells | Endpoint of cell line |
|---|---|---|---|
| 009 | pooled | STO | cultured for 3 months, injected & cryopreserved |
| 029 | pooled | insert | cultured for over 3 months, injected & cryopreserved |
| 31 | pooled | STO | injected at 4 days |
| 36 | pooled | STO | injected at 13 days |
| 50 | pooled | STO | grown for over 8 months, injected & cryopreserved |
| 63b | pooled | insert | grown for 3 months and cryopreserved |
| 67I | single | insert | injected at 45 days of culture |
| 307 | pooled | STO | injected at 15 days and fixed for staining |
| 314 | pooled | STO | cultured for over 3 months, injected & cryopreserved |
| 317 | pooled | STO | injected at 12 days and fixed for staining |
| 324A | single | insert | cultured for over 6 months and injected |
| 328 | single | insert | cultured for over 6 months, injected & cryopreserved |
| 329 | single | insert | cultured for 5 months, injected & cryopreserved |
| 330 | single | insert | cultured for 3 months and cryopreserved |
| 331 | single | 24 w insert | cultured for over 3 months and terminated |
| 332 | single | 96 w STO | cultured for 3 months and cryopreserved |
| 333 | single | 12 w insert | cultured for over 3 months and terminated |
| 334 | single | 12 w insert | cultured for over 3 months and terminated |
| 335 | single | 96 w insert | cultured for over 3 months and terminated |

Embryos are dispersed mechanically into a single cell suspension and seeded on a confluent feeder layer of mitotically inactivated STO cells at a concentration of $3 \times 10^4$ cells/cm$^2$. The cES culture medium consists of DMEM (20% fresh medium and 80% conditioned medium) supplemented with 10% FCS, 1% pen/strep; 2 mM glutamine, 1 mM pyruvate, 1× nucleosides, 1× non-essential amino acids and 0.1 mM β-mercaptoethanol. Before use, the DMEM medium is conditioned on Buffalo Rat Liver (BRL) cells. Briefly, after BRL cells are grown to confluency, DMEM containing 5% serum is added and conditioned for three days. The medium is removed and a new batch of medium conditioned for three days and repeated. The three batches are combined and used to make the cES medium. Chicken ES cells become visible 3–7 days after seeding of the blastodermal cells. These cES cells were morphologically similar to mES cells; the cells were small with a large nucleus and a pronounced nucleolus (See FIG. 1).

The growth characteristics of cES cells are different from mES cells, which grow in tight round colonies with smooth edges and individual cells that are difficult to distinguish. Chicken ES cells grow in single layer colonies with clearly visible individual cells. Tight colonies are often the first sign of differentiation in a cES culture.

To test for markers of pluripotency of the cells that were derived in culture, the cells were fixed and stained with SSEA-1 1 (Solter, D. and B. B. Knowles, Proc. Natl. Acad. Sci, U.S.A. 75: 5565–5569, 1978), EMA-1, which recognize epitopes on primordial germ cells in mice and chickens (Hahnel, A. C. and E. M. Eddy, Gamete Research 15: 25–34, 1986) and alkaline phosphatase (AP) which is also expressed by pluripotential cells. The results of these tests, which are shown in FIG. 2, demonstrate that chicken ES cells express alkaline phosphatase and the antigens recognized by SSEA-1 and EMA-1.

Although cES cells are visible after using the above protocol, such cultures cannot be maintained longer than a few weeks. Several modifications in culture conditions were initiated, as discussed below, which led to the derivation of 19 cell lines (Table 1) of which 14 were tested for their developmental potential by injection into recipient embryos. Eleven of the 14 cell lines contributed to recipient embryos as determined by feather pigmentation (See Table 2 below). This protocol yields sustained cultures of pluripotent cells expressing an embryonic stem cell phenotype. At any point, the cells can be cryopreserved and when injected into compromised recipient embryos have the potential to substantially contribute to somatic tissues (See Examples 3 and 5 below).

TABLE 2

Passage number and time in culture of embryonic stem cell lines derived from single or pooled embryos. Frequency and extent of somatic chimerism after injection of these cES cells into stage X recipients.

| Cell line | Donor embryo | Passage number | time in culture (days) | # of embryos injected | # chimeras | # analyzed | % chimeras | Extent of chemirism[1] (%) |
|---|---|---|---|---|---|---|---|---|
| 31 | pooled | 0 | 4 | 15 | 2 | 7 | 28.5 | 1–5 |
| 317 | pooled | 4 | 12 | 29 | 2 | 10 | 20 | 25–65 |
| 36 | Pooled | 1 | 13 | 24 | 1 | 5 | 20 | 15 |
| 307 | pooled | 4 | 15 | 21 | 1 | 6 | 17 | 5 |
| 330 | single | 6 | 33 | 11 | 3 | 8 | 25 | 5–50 |
| 63b | pooled | 11 | 72 | 36 | 4 | 21 | 19 | 1–10 |
| 67I | single | 3 | 45 | 28 | 0 | 15 | 0 | — |
| 324A | single | 10 | 65 | 25 | 0 | 15 | 0 | — |
| 009 | pooled | 20 | 61 | 27 | 0 | 9 | 0 | — |
| 329 | single | 3 | 15 | 31 | 8 | 17 | 47 | 3–75 |
| 329 | | 6 | 25 | 30 | 9 | 19 | 47 | 3–95 |
| 329 | | 6 | 28 | 26 | 1 | 12 | 8 | 23 |
| 329 | | 11 | 49 | 10 | 1 | 4 | 25 | 60 |
| 029 | pooled | 4 | 33 | 40 | 9 | 27 | 33 | 5–80 |
| 029 | | 9 | 37 | 40 | 4 | 15 | 27 | 4–15 |
| 328 | Single | 6 | 56 | 19 | 4 | 11 | 36 | 10–80 |
| 328 | | 12 | 98 | 33 | 7 | 22 | 32 | 5–50 |
| 314 | Pooled | 17 | 52 | 30 | 2 | 5 | 40 | 5–65 |
| 314 | | 15–17 | 53 | 29 | 1 | 4 | 25 | 30 |
| 314 | | 17 | 55 | 37 | 3 | 15 | 30 | 3–80 |
| 314 | | 16 | 65 | 27 | 2 | 11 | 18 | 5–40 |
| 314 | | 14 | 61 | 25 | 0 | 13 | 0 | — |
| 314 | | 16 | 65 | 32 | 3 | 14 | 21 | 10–60 |
| 314 | | 20 | 61 | 30 | 4 | 5 | 80 | 4–50 |
| 314 | | 21 | 67 | 30 | 2 | 11 | 18 | 5–15 |
| 314 | | 21 | 71 | 8 | 0 | 2 | 0 | — |
| 50 | pooled | 7 | 53 | 35 | 7 | 23 | 30 | 4–65 |
| 50 | | 14 | 106 | 36 | 3 | 21 | 14 | 10–30 |

[1]Extent of chimerism was determined by the proportion of black feathers.

As with the mouse, avian embryonic stem cells, which are sometimes referred to as embryonic germ cells, are derived on a variety of feeder layers including STO, STO-snl and others that are readily available. Leukemia Inhibitory Factor (LIF) produced by these feeders, and the addition of fetal bovine serum contributes to the maintenance of ES cells in an undifferentiated state. In a preferred embodiment of this invention, chicken ES cell cultures are initiated on a STO feeder layer. STO cells are grown to confluency, treated with 10 μg/ml mitomycin for 3–4 hours, washed, trypsinized and seeded on gelatin coated dishes at $4 \times 10^4$ cells/cm$^2$. cES cells appear to grow more rapidly when the feeder of STO cells are sparser. Reducing the STO feeder cell concentration to between $10^3$ and $10^5$, and preferably below $10^4$ cells/cm$^2$, facilitates the derivation and propagation of cES cells. However, when chicken embryonic fibroblasts and mouse primary fibroblasts are used as feeders, no cES cells were derived. Also, when previously established cES cells were plated on these feeders, all of them differentiated within 1 week.

Growing cES cells on synthetic inserts, such as polymer membranes (Costar, Transwell type) in the absence of feeders avoids contamination of the recipient embryo with feeder cells when the ES cells are injected. As Table 3 and 4 show, culturing on inserts, instead of STO feeders, facilitates the derivation of cES cells, and inserts can be used for initial derivation. However, after initially growing rapidly on inserts, the mitotic activity of the ES cells declines after 4–6 weeks of culture. To extend the culture the cells have to be transferred to a feeder of STO cells.

TABLE 3

Establishment of cES cells from single embryos on either inserts or a feeder of STO cells ($10^4$ cells/cm$^2$).

| Substrate | # of cultures started | # of cell lines obtained |
|---|---|---|
| STO feeder | 56 | 3 (5%) |
| insert | 45 | 7 (16%) |

TABLE 4

Establishment of cES cells from pooled embryos on either a STO feeder or a synthetic insert.

| Substrate | # of cultures started | # of cell lines obtained |
|---|---|---|
| STO feeder | 73 | 7 (9.5%) |
| insert | 17 | 2 (12%) 15 |

The data in Tables 3 and 4 show that chicken embryonic feeder cells and mouse primary fetal fibroblasts do not support the derivation or the culture of cES cells. A feeder of STO cells supports derivation and growth but only when present in a limited concentration of between $10^3$ and $10^5$ STO cells but preferably in the present embodiment at a concentration of less than or appropriately $10^4$ cells/cm$^2$. A dense STO feeder layer impairs the growth of cES cells, while the specified concentration of STO cells provides factor(s) necessary for ES cell proliferation. When the cells are sustained over an extended culture period and continue to express an embryonic stem cell phenotype, and differentiate into non-embryonic stem cell phenotypes in vivo, they are referred to as "ES cell progeny."

The cES cell culture medium consists of 80% conditioned medium and preferably contains certain BRL conditioned medium with factors necessary for the derivation and growth of cES cells. At a concentration of 50%, growth of the cES cells is not as reliable as in 80% conditioned medium. When the percentage of conditioned medium is reduced to less than 50%, the growth of the cES cells is affected, as evidenced by an increase in differentiated cells and, at a concentration of 30% or less, the cES cells differentiate within 1 week. This conditioned medium found necessary for the derivation and maintenance of cES cells does not maintain mES but causes their differentiation.

Fetal bovine serum is a preferred component of the ES cell medium according to the present invention and contains factors that keep cES cells in an undifferentiated state. However, serum is also known to contain factors that induce differentiation. Commercially available serum lots are routinely tested by users for their potential to keep ES cells in an undifferentiated state. Serum used for cES cell cultures are known to differ from serum used for mouse ES cell cultures. For example, serum used for the culture of mouse ES cells that is low in cytotoxin and hemoglobin concentration, which is known to maintain mouse ES cells in an undifferentiated state, did not support the sustained growth of chicken ES cells.

Therefore, serum to be used on chicken ES cells should not be tested on mouse ES cells to determine suitability as a media component, but instead should be evaluated on chicken ES cells. To do so, chicken ES cell cultures are divided into two and used to test each new batch of serum. The new batch tested must clearly support the growth of chicken ES cells when empirically tested.

Figure 3:
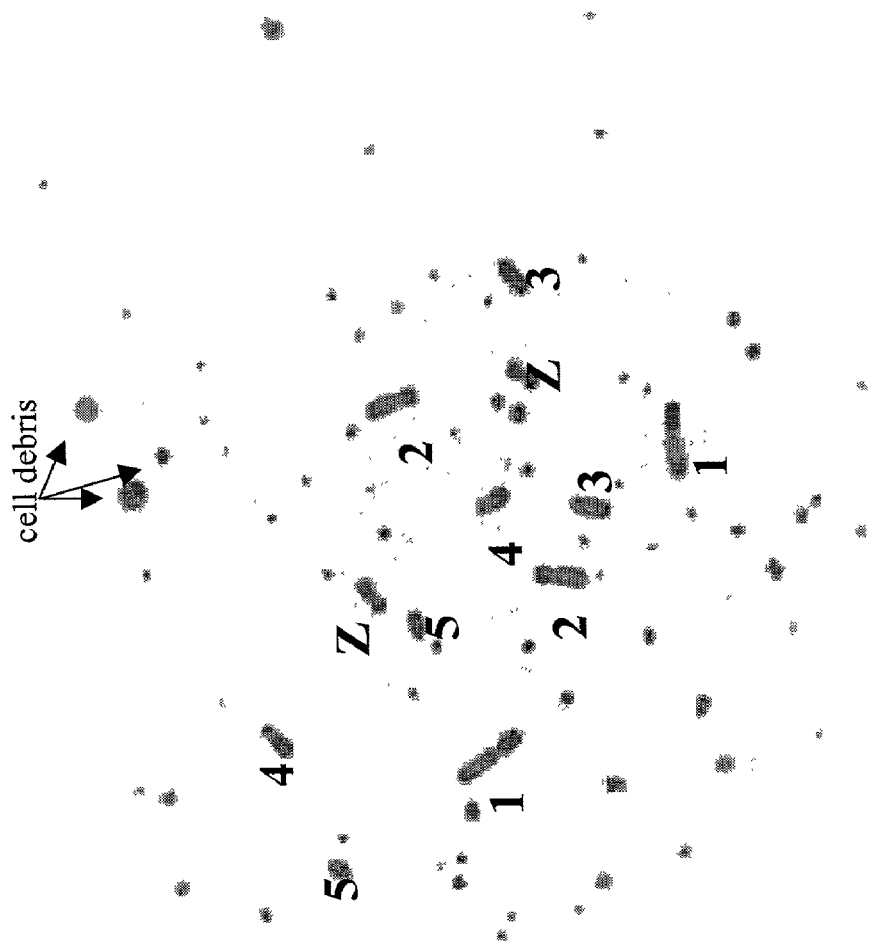
FIG. 3 is a karyotype of chicken ES cells that have been in culture for 189 days. The cells are diploid, carry 38 pairs of autosomal chromosomes and one pair of Z chromosomes.

Chicken chromosomal spreads require special evaluation techniques different than mice because the complex karyotype consisting of 10 macrochromosomes, 66 micro-chromosomes and a pair of sex chromosomes (ZZ in males and ZW in females). The long-term cES cells of the present invention shown in FIG. 3 were analyzed after 189 days in culture and being cyopreserved twice. Referring to FIG. 3, they exhibited a normal karyotype with 10 macro chromosomes; 2 Z-chromosomes and 66 microchromosomes.

Chicken ES cells are cryopreserved in 10% DMSO in medium. After thawing and injecting several cell lines into recipient embryos, somatic chimeras are obtained, indicating that the cES cells maintain their developmental potential during the cryopreservation process.

EXAMPLE 2

Injection of Chicken Embryonic Stem Cells Into Recipient Embryos

To permit access to the embryo in a freshly laid egg the shell must be breeched, inevitably leading to a reduction in the hatch rate at the end of the 21-day incubation period. The convention was to cut a small hole (less than 10 mm diameter) in the side of the egg, through which the embryo was manipulated, and re-seal with tape, a glass cover slip, shell membrane or a piece of shell. Though relatively simple to perform, this "windowing" method caused embryonic mortality between 70 and 100%. Improved access to the embryo and increased survival and hatchability can be achieved if the embryo is transferred to surrogate eggshells for incubation to hatching using two different shells and a method (adapted from Callebaut) (Callebaut, Poult. Sci 60: 723–725, 1981) and (Rowlett, K. and K. Simkiss, J. Exp. Biol. 143: 529–536, 1989), which are specifically incorporated herein by reference with this technique, the mean hatch rate is approximately 41% (range 23–70%) with 191 chicks hatched from 469 cES-cell injected embryos.

Incubation of embryos following injection of donor ES cells into recipient embryos can be divided into two parts comprising System A and System B as described below:

System A covers the first three days of post-oviposition development. Fertile eggs containing the recipient embryos are matched with eggs 3 to 5 grams heavier. A 32 mm diameter window is cut at the pointed pole, the contents removed and the recipient embryo on the yolk, together with the surrounding albumen, is carefully transferred into the surrogate shell.

Cells are taken up in a sterile, finely tapered glass pipette connected to a mouth aspirator fitted with a 2 micron filter. The opening of the pipette can be from 50 to 120 microns in diameter and possesses a 30° spiked bevel. The embryo is visualized under low magnification and with blue light. Chicken ES cells are trypsinized into a single cell suspension and 4,000 to 26,000 cells are injected into an embryo. The cells are gently expelled into the space either below or above the embryo, i.e. into the sub-embryonic cavity or between the apical surface of the area pellucida and the perivitelline layer (yolk membrane). Extra albumen collected from fresh fertile eggs is added and the shell sealed with Saran Wrap plastic film.

System B covers the period from day three to hatching. At day three of incubation the embryo has reached around stage 17 (H&H). Water has been transported from the albumen to the sub-embryonic cavity, causing the yolk to enlarge and become very fragile. The contents of the System A shell are very carefully transferred to a second surrogate shell (usually a turkey egg) 30 to 35 grams heavier than the original egg. Penicillin and streptomycin are added to prevent bacterial contamination and the 38 to 42 mm window in the blunt pole is sealed with plastic film. This larger shell allows for an artificial airspace. At day 18 to 19 of incubation the embryo cultures are transferred to tabletop hatchers for close observation. As lung ventilation becomes established, holes are periodically made in the plastic film to allow ambient air into the airspace. Approximately 6–12 hours before hatching the film is replaced with a small petri dish, which the chick can easily push aside during hatching.

For incubation, conventional temperature (37.5 to 38° C.) and relative humidity (50 to 60%) are maintained for the embryos in surrogate shells, but periodic egg rocking, which is normally hourly and through 90 degrees, has to be modified to ensure good survival. In System A rocking is through 90° every 4 to 5 minutes; in System B it is through 40 to 60° every 40 to 45 minutes. In both systems the speed of rocking is maintained at 15 to 20° per minute.

Figure 4:
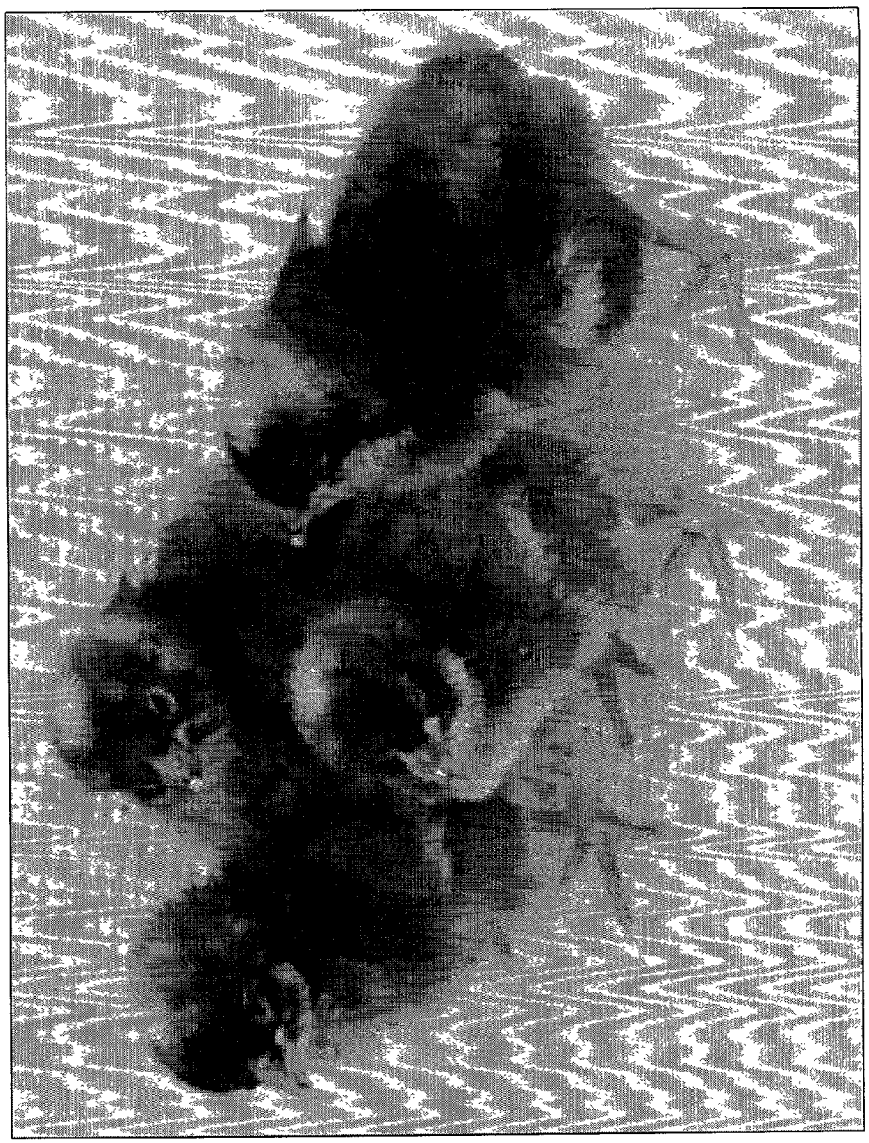
FIG. 4 is two Barred Rock chicks and two chimeras formed by injecting Barred Rock ES cells into a White Leghorn recipient embryo. The chimeras and the Barred Rocks are indistinguishable indicating that the contributions of the ES cells to the melanocyte lineage is extensive.

The contribution of cES cells to chimeras is improved if the recipient embryo is prepared by (1) irradiated by exposure to 660 rads of gamma irradiation (2) altered by mechanically removing approximately 1000 cells from the center of the embryo, or by combining (1) and (2) above before the injection of the cES cells. Referring to Table 5, contribution of cES cells to the somatic tissues increased substantially when recipient embryos were compromised, either by removing cells from the center of the recipient embryo or by exposure to irradiation. When the recipient embryos are compromised by a combination of irradiation and mechanical removal of the cells, the contribution of the ES cells is increased further, even though the cES cells had been in culture for longer periods of time. Some of the resulting chimeric chicks are indistinguishable from pure Barred Rock chicks (FIG. 4). As the data in Table 5 show, chimerism rates as well as the extent of chimerism per embryo increases after compromising the recipient embryo.

of embryos (83/347) are chimeric as determined by feather color. Feather chimeras are obtained from 11/14 cell lines. The extent of chimerism varied from 1%–95% with a mean extent of 25.9% (SD=20.4).

Figure 5:
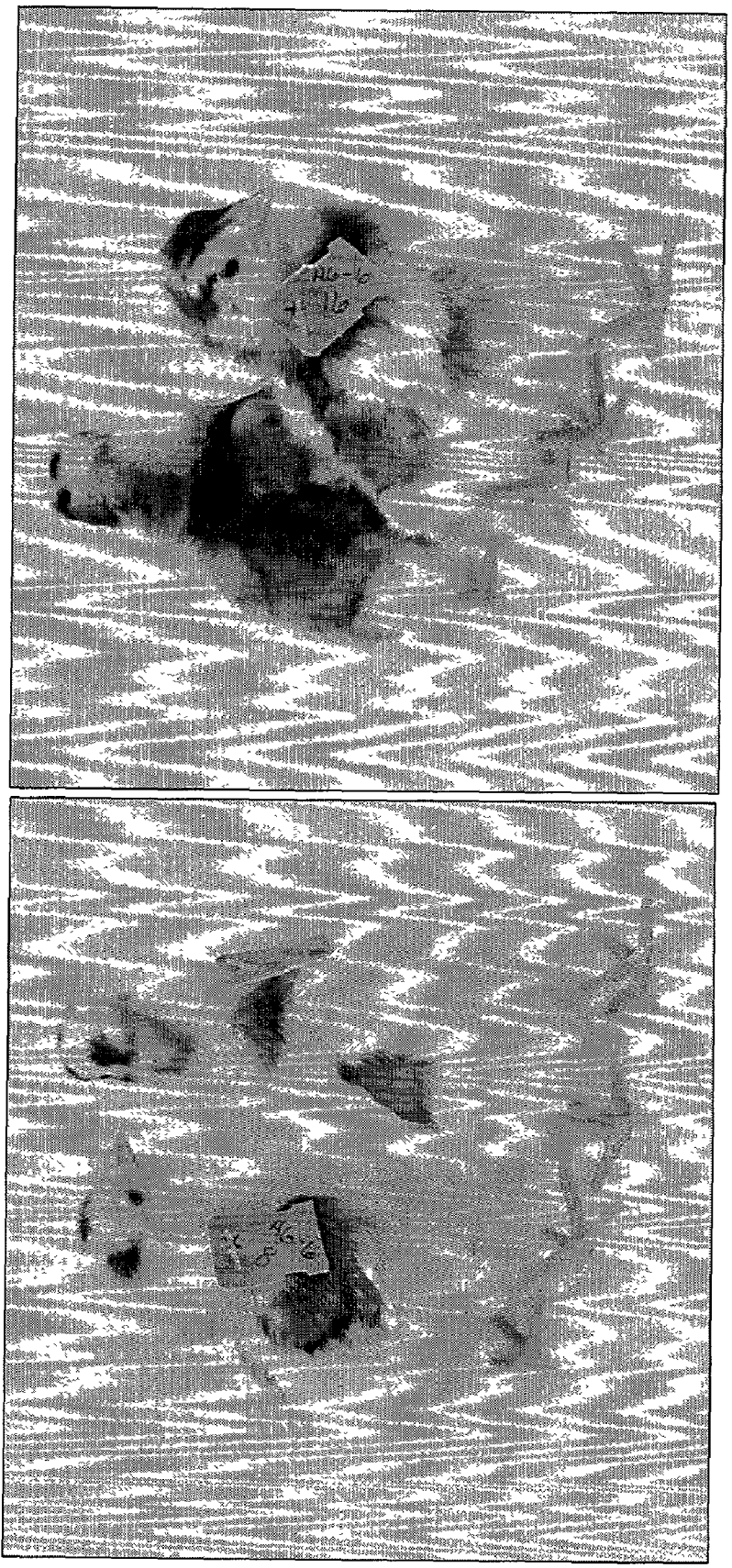
FIG. 5 are chimeras made by injecting Barred Rock ES cells into White Leghorn recipients. The pair of chimeras in the left panel exhibit minor contributions to the melanocyte lineage whereas the pair in the left panel show more extensive contributions.

Table 2 illustrates the variance in the somatic chimerism between experiments performed within and between cell lines. Examples of the contribution of ES cells to chimeras is shown in FIGS. 4 and 5. In FIG. 4, two chicks are chimeras and two are Barred Rocks; it is apparent that there are no phenotypic differences between these chicks indicating that the contribution of ES cells to the chimera is extensive, particularly in the ectodermally derived lineages. In FIG. 5, the chimeras on the left have relatively low levels of contribution from ES cells whereas those on the right have intermediate contributions.

TABLE 5

Frequency of somatic chimerism after injection of cES cells into recipient embryos that were compromised by different methods.

| Treatment to compromise the recipient embryo | # Cell lines | Time cells in culture | # Chimeras | # Embryos & chicks evaluated | Frequency of chimerism % | Extent feather chimerism (%) |
|---|---|---|---|---|---|---|
| None | 14 | 4–106 days | 83 | 347 | 24 | 26 |
| Mechanical removal of cells | 1 | 6 months | 34 | 63 | 54 | 20 |
| Irradiation | 1 | 6–7 months | 56 | 95 | 59 | 29 |
| Irradiation & Mechanical removal of cells | 1 | 7–8 months | 52 | 59 | 88 | 49 |

Recipient embryos substantially younger than stage X may also be used to produce chimeras using ES cell as the donor. Early stage recipient embryos are retrieved by injecting the hens with oxytocin to induce premature oviposition and fertile eggs are retrieved at stages VII to IX.

Alternatively, the retrieval of embryos from the magnum region of the oviduct provides access to stage I to VI embryos, consisting of approximately 4–250 cells, and enables the development of chimeras from all embryonic stages as potential recipient embryos.

EXAMPLE 3

Somatic Chimeras From Chicken Embryonic Stem Cells (CES)

To demonstrate that pluripotency of the cES cells of the invention, cES cells are injected into White Leghorn recipient embryos. In the first round of experiments, a total of 14 cell lines in 28 experiments are injected into stage X recipient embryos (See Table 2). The cES cells have been propagated in culture between 4 and 106 days and some lines had been cryopreserved. Chicken ES cells are lightly trypsinized, resulting in small clumps of cES cells, and resuspended in DMEM supplemented with 25 mM HEPES+ 10% fetal calf serum. Three to five μl of the cell suspension, containing between 2000–5000 cells, are injected into the subgerminal cavity of the recipient embryos. All embryos that developed feathers are analyzed and twenty four percent

EXAMPLE 4

Transfection of CES Cells By Lipofection and Electroporation

Referring to Table 6, an appropriate amount of DNA compatible with the size of the well being transfected is diluted in media absent of serum or antibiotics. The appropriate volume of Superfect (Stratagene) is added and mixed with the DNA, and the reaction is allowed to occur for 5–10 minutes. The media is removed and the wells to be transfected are washed with a Ca/Mg free salt solution. The appropriate volume of media, which can contain serum and antibiotics, is added to the DNA/superfect mixture. The plates are incubated for 2–3 hours at 37C. When the incubation is completed, the Superfect is removed by washing the cells 1–2× and fresh culture media is added.

TABLE 6

Conditions for transfection of chicken ES cells using Superfect.

| Plate Size | Volume of media used to dilute DNA | Total amount of DNA | ul Superfect | Time to form complex (min) | Volume of media added to complex | Incubation time |
|---|---|---|---|---|---|---|
| 96 well | 30 ul | 1 | 5 ul | 5–10 | 150 | 2–3 hrs |
| 48 well | 50 ul | 1.5 | 9 ul | 5–10 | 250 ul | 2–3 hrs |
| 24 well | 60 ul | 2 | 10 ul | 5–10 | 350 ul | 2–3 hrs |
| 12 well | 75 ul | 3 | 15 ul | 5–10 | 400 ul | 2–3 hrs |
| 6 well | 100 ul | 4 | 20 ul | 5–10 | 600 ul | 2–3 hrs |

TABLE 6-continued

Conditions for transfection of chicken ES cells using Superfect.

| Plate Size | Volume of media used to dilute DNA | Total amount of DNA | ul Superfect | Time to form complex (min) | Volume of media added to complex | Incubation time |
|---|---|---|---|---|---|---|
| 60 mm | 150 ul | 10 | 50 ul | 5–10 | 1000 ul | 2–3 hrs |
| 100 mm | 300 ul | 20 | 120 ul | 5–10 | 3000 ul | 2–3 hrs |

A petri-pulser is used to electroporate cES cells that are attached to the plate in a 35 mm 5 diameter well. The media is removed and the well is washed with a salt solution without $Ca^{++}$ and $Mg^{++}$. One ml of electroporation solution is added to the well. DNA is added and the media is gently mixed. The petri-pulser is lowered onto the bottom of the well and an electrical current is delivered. (Voltage preferably varies from 100–500 V/cm and the pulse length can be from 12–16 msec). The petri-pulser is removed and the electroporated well is allowed to stand 10 for 10 minutes at room temperature. After 10 minutes, 2 mls of media is added and the dish is returned to the incubator.

To transfect cells in suspension, media is removed and cells are washed with a Ca/Mg free salt solution. Tryspin with EDTA is added to obtain a single cell suspension. Cells are washed, centrifuged and resuspended in a correctional electroporation buffer solution such as PBS. The ES cell suspension is placed into a sterile cuvette, and DNA added (minimum concentration of 1 mg/ml) to the cell suspension and mixed by pipetting up and down. The cells are electroporated and allowed to sit at RT for 10 minutes. Cells are removed from cuvette and distributed to previously prepared wells/dishes. Cells are placed in an incubator and evaluated or transient transfection 24–48 hours after electroporation. Selection of antibiotic resistant cells may also be started by including an antibiotic such as puromycin in the culture medium.

In a preferred embodiment, the concentration of puromycin required for selecting transfected cells is calculated as a titration kill curve. Titration kill curves for chicken embryonic stem cells are established by exposing cells in culture to puromycin concentrations varying from 0.0 to 1.0 µg/ml for 10 days (Table 7) and neomycin concentrations varying from 0.0 to 200 ug/ml (Table 8). The medium is changed every 2 days and fresh puromycin or neomycin is added. When exposed to a concentration of 0.3 µg/ml puromycin, ES cells were absent from all wells after 3 changes of medium with fresh puromycin over a six day period (see Table 7). Puromycin concentrations of 0.3–1.0 µg/ml are used for selection of the transfected cultures. Neomycin concentrations over 40 µg/ml eliminated all cES cells within 7 days (Table 8).

After 10 days of selection, cES cells colonies are visible and can be picked for further expansion.

TABLE 7

Morphology of cES cells after exposure of various concentrations of puromycin and different lengths of time (days after addition of puromycin).

| Puromycin conc. (µg/ml) | Time under selection (days) | | | | | | | | | |
|---|---|---|---|---|---|---|---|---|---|---|
| | 1 | 2 | 3 | 4 | 5 | 6 | 7 | 8 | 9 | 10 |
| 0.0 | ES | ES | ES | ES | ES | ES | ES | ES | ES | ES |
| 0.1 | ES | ES | ES | ES | ES | ES | ES | ES | ES | ES |
| 0.2 | ES | ES | ES | ES | ES | ES | ES | ES | ES | ES |
| 0.25 | ES | ES | ES | ES | ES | diff | diff | diff/gone | diff/gone | diff/gone |
| 0.3 | ES | ES | diff | diff/gone | diff/gone | gone | gone | gone | gone | gone |
| 0.4 | ES | diff | gone | gone | gone | gone | gone | gone | gone | gone |
| 0.5 | diff | gone | Gone | gone | gone | gone | gone | gone | gone | gone |
| 0.6 | diff | gone | gone | gone | gone | gone | gone | gone | gone | gone |
| 0.7 | diff | gone | gone | gone | gone | gone | gone | gone | gone | gone |
| 0.8 | gone | gone | gone | gone | gone | gone | gone | gone | gone | gone |

ES: ES cells are present.
diff: ES cells are differentiated.
gone: no morphologically recognizable cells are present

TABLE 8

Morphology of cES cells after exposure of various concentrations of neomycin and different lengths of time (days after addition of neomycin).

| Neomycin conc. (μg/ml) | Time under selection (days) | | | | | | | | | |
|---|---|---|---|---|---|---|---|---|---|---|
| | 1 | 2 | 3 | 4 | 5 | 6 | 7 | 8 | 9 | 10 |
| 0.0 | ES | ES | ES | ES | ES | ES | ES | ES | ES | ES |
| 10 | ES | ES | ES | ES | ES | ES | ES | ES | ES | ES |
| 20 | ES | ES | ES | ES | ES | ES | ES | ES | ES | ES |
| 30 | ES | ES | ES | ES | ES | ES | ES/Diff | ES/diff | Diff | Diff/gone |
| 40 | ES | ES | ES | ES | ES/Diff | Diff/dead | dead | gone | gone | gone |
| 50 | ES | ES | ES | ES/Diff | ES/Diff | Diff/dead | Dead/gone | gone | gone | gone |
| 60 | ES | ES | ES | gone | gone | gone | gone | gone | gone | gone |
| 100 | ES/Diff | Diff | dead | gone | gone | gone | gone | gone | gone | gone |
| 150 | | dead | dead | gone | gone | gone | gone | gone | gone | gone |
| 200 | | dead | gone | gone | gone | gone | gone | gone | gone | gone |

Selection of transfected chicken ES cells and their identification in chimeras requires that the transgene confer a selective advantage to the cells in culture (e.g. resistance to puromycin in the medium) and that it produce an identifiable gene product in the cells in the chimera which are derived from the ES cells. This can be accomplished using pCX/GFP/Puro which provides resistance to puromycin in cES cells and produces a green fluorescent protein (GFP) in most, if not all, donor-derived cells in chimeras.

Figure 6:
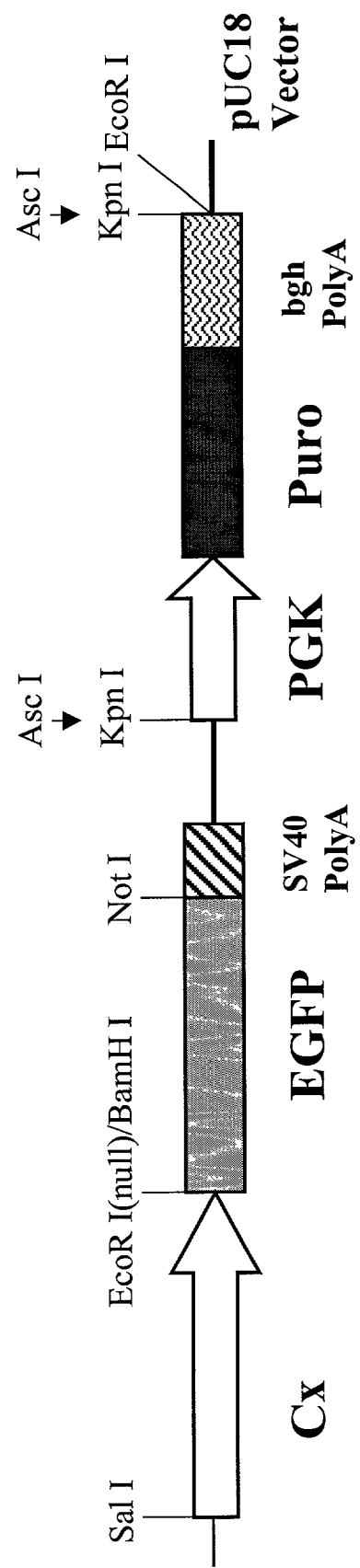
FIG. 6 is a diagram of the pCX/GFP/Puro plasmid construct used for transfection of ES cells.

Referring to FIG. 6, PCX/GFP/Puro (FIG. 6) was produced in three cloning steps involving two intermediates before make the final pCX/GFP/Puro plasmid. In step 1, the PGK-driven Puromycin resistant gene cassette (1.5 Kb) was released from pKO SelectPuro (Stratagene) by Asc I digestion. The fragment was then blunted and Kpn I linkers were added. The resulting fragment (GFP/Puro) was inserted into the corresponding Kpn I site of pMIEM (courtesy of Jim Petitte (NCSU), a GFP expression version derived from LacZ expression pMIWZ, see *Cell Diff and Dev.* 29: 181–186 (1990) to produce the first intermediate (pGFP/Puro). The PGK-Puro cassette was in same transcription orientation as GFP (determined by BamH I and Sty I digestion). In step 2, the GFP/Puro expression cassette (2.5 Kb) was released from pGFP/Puro by BamH I and EcoR I double digestion. The resulting fragment was inserted into the BamH I and EcoR I sites of pUC 18 (Invitrogen). It contains 5' unique sites, Hind III, Pst I and Sal I. The resulting plasmid pUC 18/GFP/Puro was verified by a BamH I, EcoR I, and Not I triple digestion. In the third step, the Cx promoter including 384 bp CMV-IE enhancer, 1.3 kb chicken beta-actin promoter and portion of 1$^{st}$ intron was released from pCX-EGFP (Masahito, I. et al., FEBS Letters 375: 125–128, 1995) by Sal I and EcoR I digestion. A 3' EcoR I (null)-Xmn I-Bam-H I linker was attached to the fragment and it was inserted into the Sal I and BamH I sites of pUC18/GFP/Puro. The plasmid pCX/GFP/Puro (FIG. 6) was verified by a BamH I and Pst I double digestion. pCX/GFP/Puro DNA can be linearized by Sca I digestion for transfection into cES cells.

Figure 7:
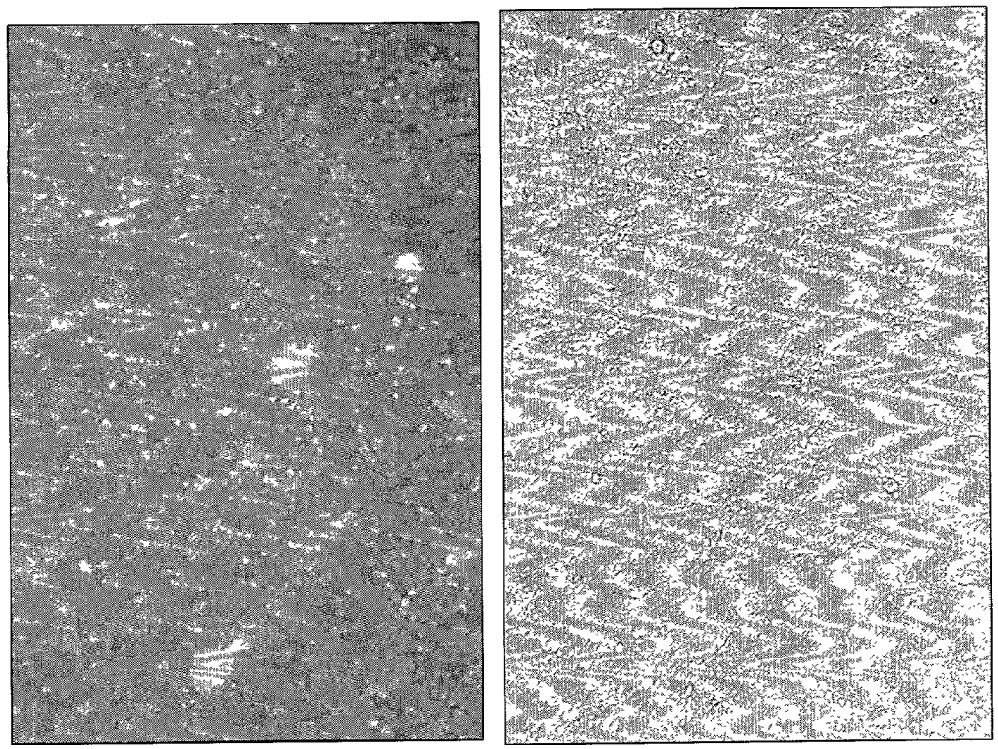
FIG. 7 shows chicken ES cells that have been transfected with the pCX/GFP/Puro construct and grown in the presence of puromycin. The upper panel is photographed to reveal fluorescence; the lower panel is the same field viewed by phase contrast microscopy.
Figure 8:
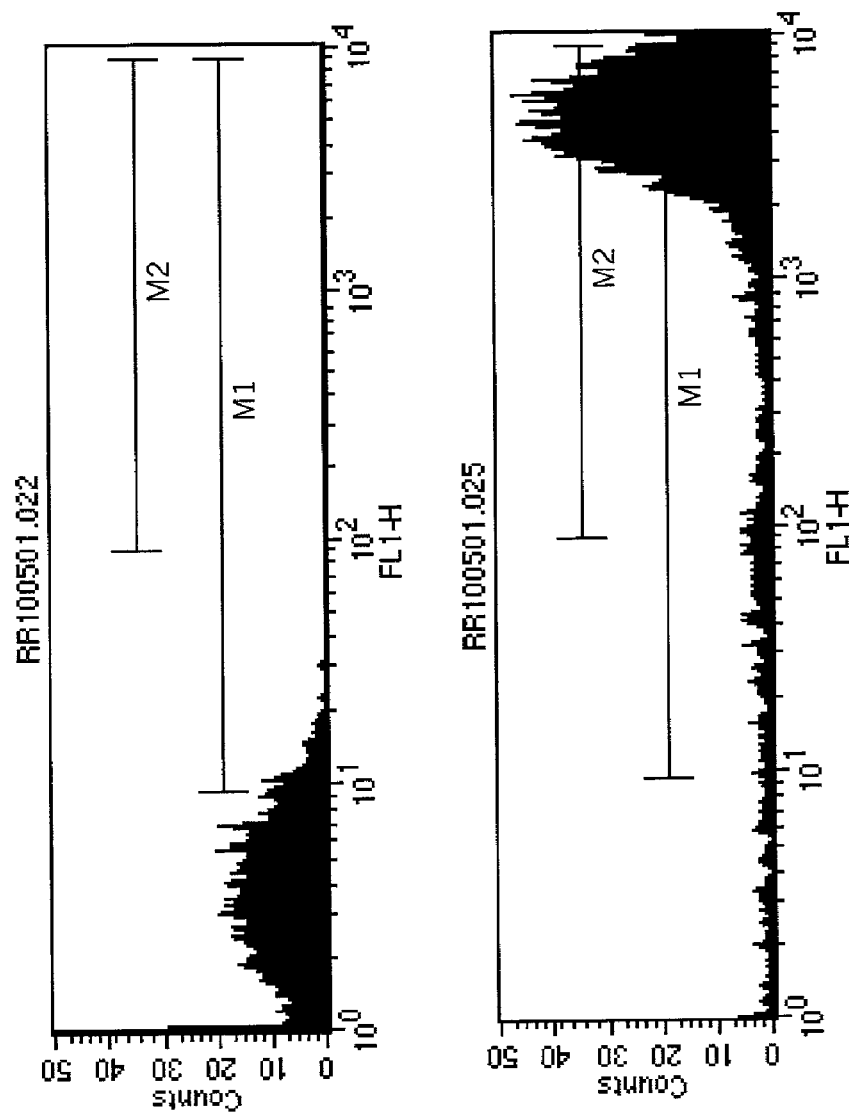
FIG. 8 is a FACS analysis of non-transfected chicken ES cells (upper panel) and chicken ES cells that have been transfected with the pCX/GFP/Puro construct and grown in the presence of puromycin. The analysis shows that substantially all of the transfected cells are expressing the transgene.
Figure 9:
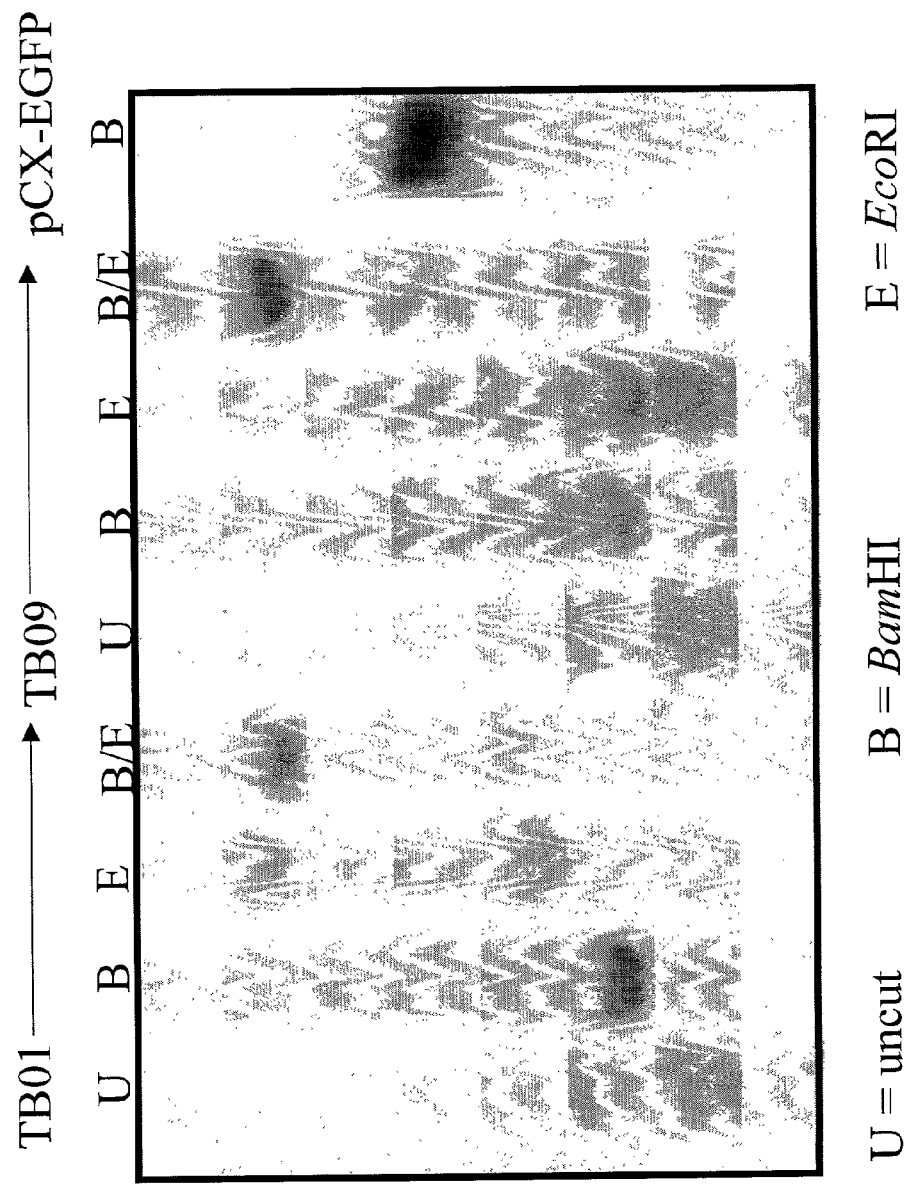
FIG. 9 is a Southern analysis of ES cells that have been transfected with the pCX/GFP/Puro construct. The difference in the location of the probe in preparations of DNA digested with BamH1, EcoR1 and a combination of the two endonucleases indicates that the transgene in incorporated into the genome at different sites in the cell lines TB01 and TB09.

Transfection and selection of ES cells using the procedures described above produced a population of cells that would grow in the presence of 0.5 ug of puromycin. These cells exhibited green fluorescence when examined by conventional fluorescence microscopy (See FIG. 7). When preparations of the ES cells are examined by fluorescence activated cell sorting, it is evident that essentially all of the cells carry and express the transgene (See FIG. 8). Southern analysis of DNA from the transfected ES cell lines TB01 and TB09 that was digested with BamH1, EcoRI or both restriction endonucleases revealed the transgene in DNA fragments of various sizes, providing evidence that the transgene is integrated into the genome (See FIG. 9).

The CX/GFP/Puro construct demonstrates that transgenes of at least 4.5 kb can be inserted into chimeric chickens. Using the cES cells described herein, chicken ES cells can be transfected with different or larger constructs. In the preferred embodiments of the invention, the transgene is comprised of DNA encoding an exogenous protein that is present and widely distributed in somatic cells of the resulting chimeric or transgenic animal. Preferably, the transgene is present and expressed in any or all of the endoderm, mesoderm, ectoderm, and extra embryonic tissue. The DNA encoding the exogenous protein is preferably expressed in the tissue types such that the exogenous protein is detectable in the specific cell types.

In another example, ovalbumin contructs that are designed to express significant levels of rearranged immunoglobulin molecules in the tubular gland cells of the magnum region of the oviduct, have been prepared, inserted into ES cells and used to make chimeras. The ovalbumin-derived monoclonal antibody expression constructs, which contain 42 to 49 kb of DNA, were designed as follows:

A chicken genomic BAC library (Crooijmans, R. P. et al., Mamm. Genome 11: 360–363, 2000), (Texas A & M BAC Center) is screened to isolate a region of 46 Kb in the Ovalbumin locus.

Figure 10A:
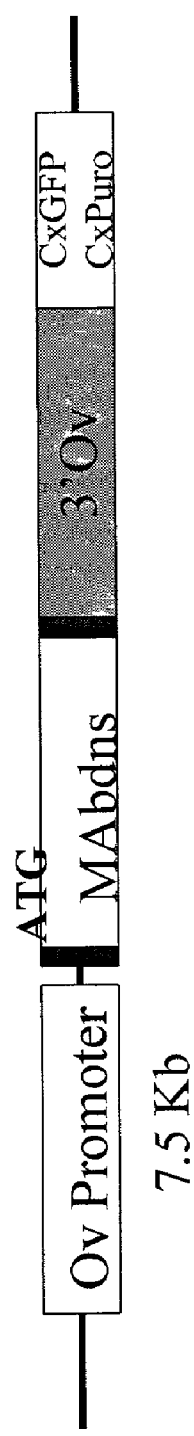

Two ovalbumin-derived expression vectors are constructed based on above identified sequences:

(1) Ov7.5MAbdns A 42 Kb expression vector contains 9.2 Kb 5' sequences from the ovalbumin gene (including 7.5 Kb promoter) and 15.5 Kb 3' flanking sequences (FIG. 10A). Tis 42 kb expression vector contains 9.2 kb of 5' sequence from the ovalbumin gene (including 7.5 kb promoter) and 15.5 kb 3' flanking sequences. A bicistronic monoclonal antibody cassette encodes the light chain, an IRES and the heavy chain of an anti-dansyl antibody.

Figure 10B:
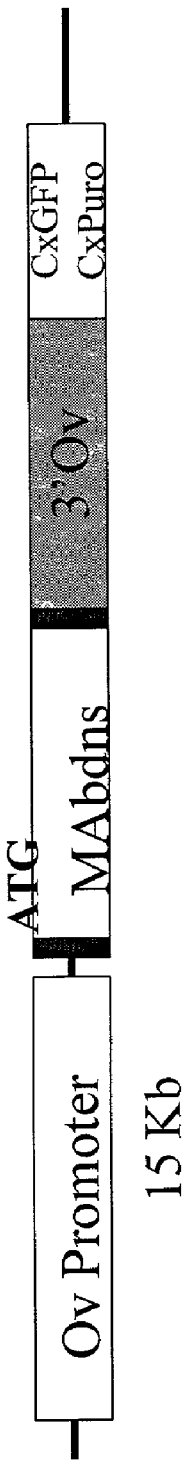

(2) Ov15MAbdns A 49 Kb expression vector contains 16.8 Kb 5' sequences from the ovalbumin gene (including 15 Kb promoter) and 15.5 Kb 3' flanking sequences (FIG. 10B). The 49 kb expression vector contains 16.8 kb of 5' sequence from the ovalalbumin gene (including 15 kb promoter) and 15.5 kb3' flanking sequences. The monoclonal antibody cassette is identical to that shown in the upper panel.

The gene to be expressed in both vectors is a mouse-human hybrid anti-dansyl monoclonal antibody (MAbdns). A CxEGFP/CxPuro cassette is cloned in the most 3' end to allow selection with puromycin for stable transfection in cES cells and easy identification of transfected cells in chimeras. Both constructs are linearized and purified before transfection into cES cells.

Transfections of cES cells are performed with Ov7.5MAbdns and Ov15MAb using either SuperFect (Stratagene) or petri-pulser electrop oration. After selection with puromycin, 6 resistant clones are picked for molecular analysis. The presence of the transgene is evident by PCR with primers located in the MAbdns cassette, in the GFP gene and in the Puro gene.

In yet another example, a very large transgene encoding part of the unrearranged human heavy chain immunoglobulin locus has been transfected into chicken ES cells. A 139 kilobase bacterial artificial chromosome (BAC) clone was co-transfected with the pCX-EGFP-CX-puro selectable marker into cES cells by co-lipofection of circular BAC DNA and linear selectable marker DNA. The BAC clone contains a human genomic DNA insert from an unrearranged immunoglobulin heavy chain locus and contains the most 3' variable region ($V_H6$-1), all the diversity (D) segments, all the joining (J) segments, the Cmu and Cgamma constant regions, the J-intronic enhancer, and all the intervening DNA between these elements. It also includes the human gene KIAA0125, a gene that encodes a non-translated RNA of unknown function that is found between $V_H6$-1 and the D segment region. pCX-EGFP-CX-puro is a plasmid that contains the Enhanced Green Fluorescent Protein (EGFP) gene driven by the CX promoter (consisting of a cytomegalovirus enhancer and the chicken β-actin promoter) and a puromycin resistance gene driven by the same promoter. The cES cells transfected with this plasmid are green fluorescent and resistant to the antibiotic puromycin. The presence of the unrearranged human heavy chain locus in the transfected ES cells that were growing in the presence of puromycin was examined by PCR analysis of transgenes spread throughout the 139 kb construct. The primer sequences used in the PCR analysis were:

```
V<sub>H</sub>6-1.
V6-1F     AGTGTCAGGGAGATGCCGTATTCA    SEQ ID NO:1
V6-1R     ACTTCCCCTCACTGTGTCTCTTG     SEQ ID NO:2

D1-26:
D1-26F    GGGCGCCTGGGTGGATTCTGA       SEQ ID NO:3
D1-26R    GTGGCCCCTAAACCTGAGTCTGCT    SEQ ID NO:4

D1-20:
D1-20F    CCCGAGCACCGTCCCCATTGA       SEQ ID NO:5
D1-20R    GTGCCGGTGATCCCTGTCTTTCTG    SEQ ID NO:6

Cμ:
Mu1F      GCGGGAGTCGGCCACCATCACG      SEQ ID NO:7
Mu1R      AGCACAGCCGCCGCCCCAGTAG      SEQ ID NO:8

Cδ:
Delta1F   TGGGGAGAGGAGAGCACAGT        SEQ ID NO:9
Delta1R   GGCGGGCGTAGGGGTCAGC         SEQ ID NO:10
``` cES cells are co-transfected with the selectable marker pCX-EGFP-CX-puro and the BAC CTD-2005N2, resulting in a cES cell line designated BAC-A. Genomic DNA is prepared and PCR performed using 5 different primer sets corresponding to markers along the length of the BAC clone. These markers are: $V_H6$-1 (24 kb from the 5' end [relative to the human heavy chain locus] of the human genomic insert), D1-26 (83 kb from the end), D1-20 (73 kb from the end), Cμ(~108 kb from the end), and Cδ(~120 kb from the end). Only $V_H6$-1, Cμ, and D1-26 are shown but all gave similar results. As a control for amplification from the cES cell sample, a chicken β-actin PCR is also run. The samples are:
1. BAC-A cells;
2. Mouse STO cells used as a feeder layer for the cES cells (negative control);
3. Barred Rock embryo DNA (the same strain a the parental cES cell line, negative control);
4. Human genomic DNA (positive control);
5. cES cell medium (negative control).

Figure 11:
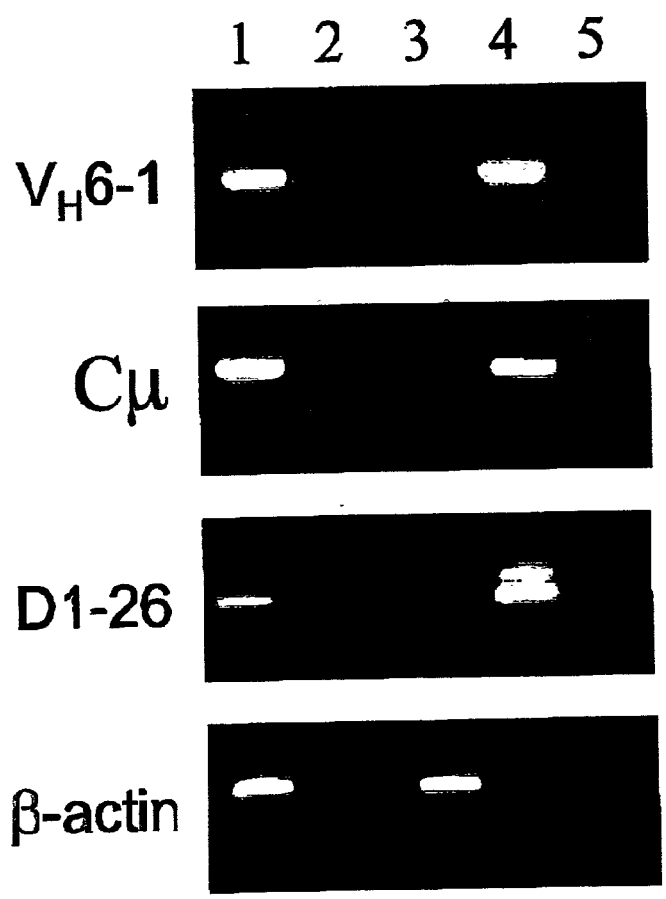
FIG. 11 is the genomic PCR analysis of BAC-A transfected cES cells.

As shown in FIG. 11, all segments of the transgene are present in the transfected and selected ES cells.

EXAMPLE 5

Identification of Transfected Donor-Derived Cells in Chimeras

Figure 12:
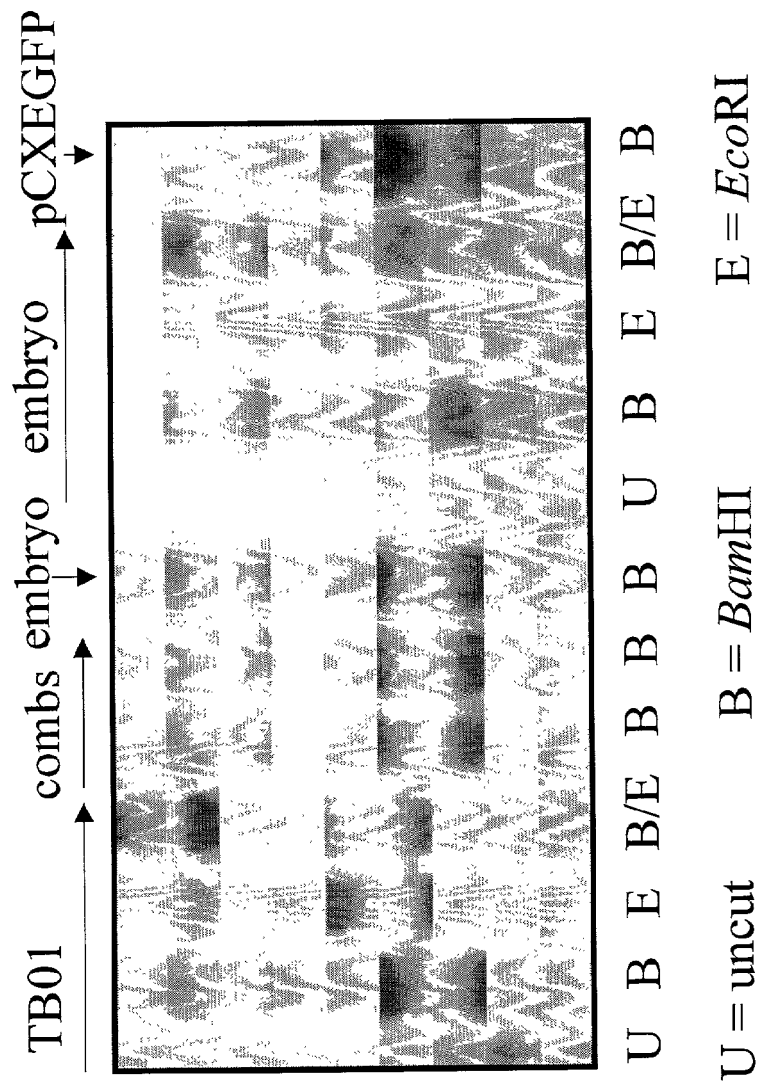
FIG. 12 is a Southern analysis of chimeras made with cES cells transfected with CX/GFP/Puro.

Transfected donor derived cells are detected in chimeras by a number of methods. For example, the transgene is detected by Southern analysis of tissue taken from chimeras that are identified by the presence of black pigmentation in their feathers. Also, DNA is harvested from embryos or from comb tissue and digested with BamH1, EcoR1 or a combination of these endonucleases. When DNA from tissues in the chimeras are examined by Southern analysis, bands that were identical to those seen in TB01, which was the donor cell used to make the chimeras, were evident after digestion with either BamH1, EcoR1 or a combination of these two restriction endonucleases (FIG. 12), thus providing evidence that the chimera contains progeny of the ES cells that were introduced into the recipient embryo to form the chimera.

Figure 14:
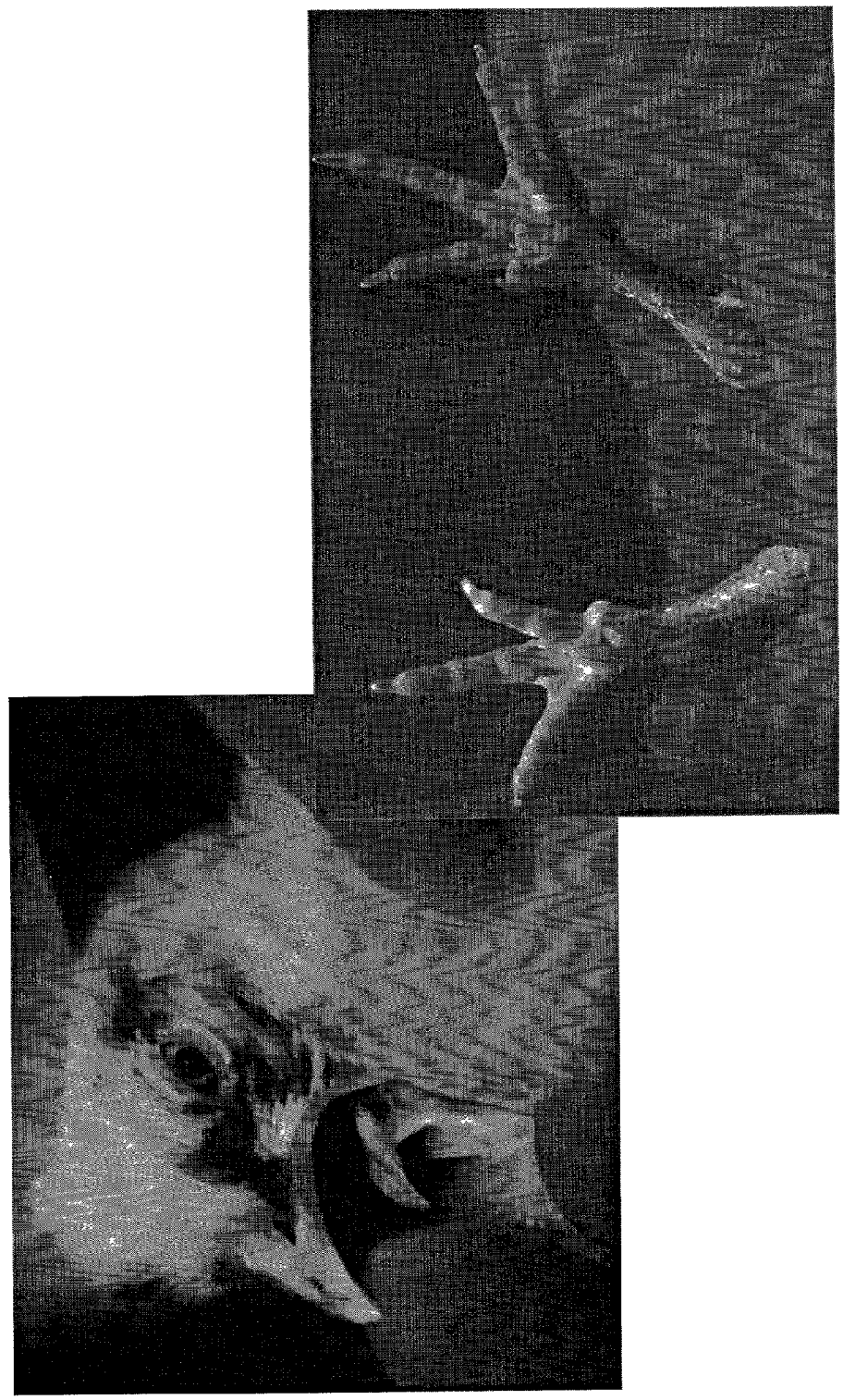
FIG. 14 is a photograph of a chimeric chicken made with cES cells transfected with CX/GFP/Puro under fluorescent light. The green fluorescence in the buccal cavity, legs, and feet show that the ES cells contributed to these tissues.

The presence of the transgene in tissues is detected by illuminating the chimeras with fluorescent lights, which shows that the transgene is expressed in the eye and the beak (FIG. 13), the buccal cavity, legs and feet (FIG. 14), and in the bones of the wing and in cells in the feather pulp (FIG. 15). Examination of the internal organs revealed that donor-derived ES cells had contributed to the intestinal tissues and breast muscle (FIG. 16) and leg muscle (FIG. 17). In another bird, extensive contributions to the pancreas were observed (FIG. 18). These data provide compelling evidence that the progeny of ES cells contribute to the ectoderm which gives rise to the beak, feathers and skin, to the mesoderm which gives rise to muscle and bone and to the endoderm, which gives rise to the pancreas.

Figure 19:
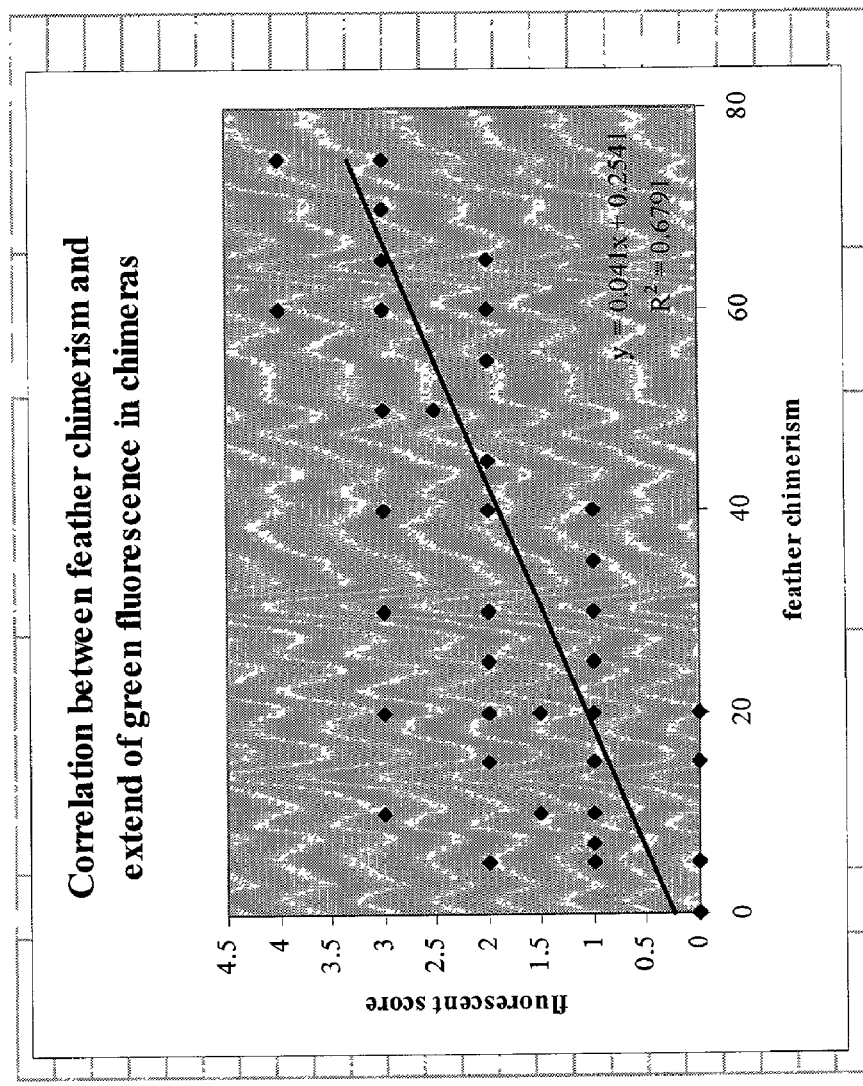
FIG. 19 shows the correlation between estimates of chimerism derived by scoring the level of fluorescence in skin and comb tissues and derived by scoring the extent of black pigmentation of the chick at hatch.

Illumination of the bird with fluorescent light is used to score the birds on a scale of 1 to 4 where 4 indicates that all of the visible skin, eyes and comb are fluorescent. The fluorescent score was determined by screening several areas of the skin with a fluorescent lamp and scoring the chicks on a scale of 0 to 4. A similar score is used to rate the extent of chimerism estimated by feather pigmentation. Feather chimerism was estimated as % of black down compared to down at hatch. Approximately 25% of the down of a Barred Rock chick is white. The maximum score that is possible in a chimera derived completely from Barred Rock derived ES cells is, therefore, 75%. The correlation between the two which is described by the equation $y=0.4x+0.25$ where y is the fluorescence score and x is the extent of ES-cell derived feather pigmentation is shown in FIG. 19.

Figure 20:
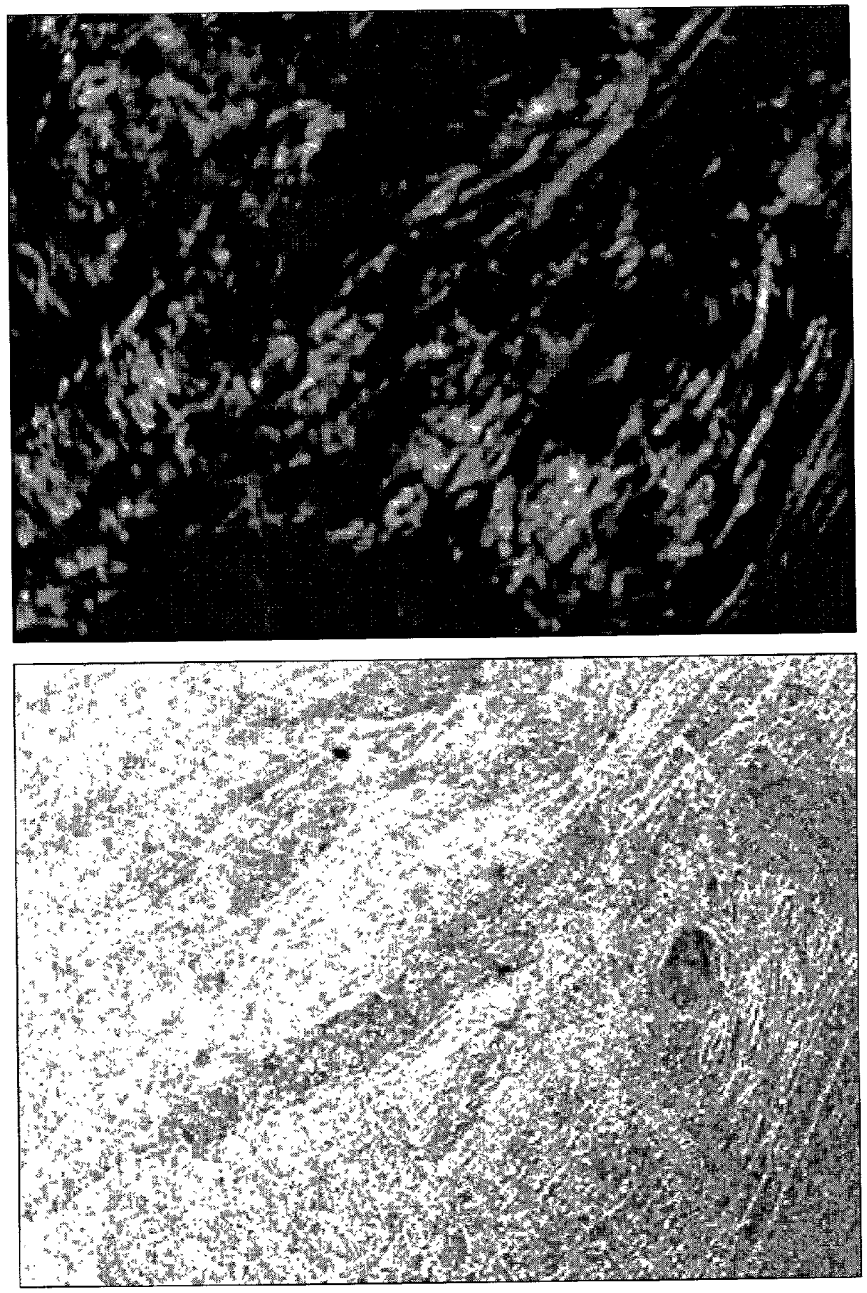
FIG. 20 is a photograph of the allantois of a chimeric embryo made with cES cells transfected with CX/GFP/Puro under fluorescent light (left panel) and white light (right panel). The green fluorescence in the allantois demonstrates that ES cells contributed to this tissue.

Examination of the chorioallantois indicated that cES cells also contributed to the extraembryonic tissues (See FIG. 20). These data indicate that the pluripotentiality of chicken ES cells may be greater than that of murine ES cells, which do not contribute to the trophectoderm.

In addition to examination of live tissues in chimeras, cells were prepared from a variety of tissues and the proportion of ES-cell derived fluorescing cells was determined. Tissue (muscle, liver or brain) was removed from chickens post-mortem, then rinsed with PBS to remove blood or other fluids. The outer membrane of the tissue was dissected away and the remaining sample was minced. Each tissue sample was transferred to a microcentrifuge tube containing 1 ml of 1 mg/ml collagenase (Type IV, Sigma) in either DMEM (muscle and liver) or Liebovitz L15 medium (brain) without serum. These tubes were incubated in a 37° C. water bath for 30–45 minutes (the tubes were inverted every 10–15 minutes to shake the suspension) and then the tissues were dispersed into single cell suspensions using a 100–200 ul pipette equipped with a disposable plastic tip and purified according to the tissue type. All centrifugation steps were executed in a microcentrifuge.

For the muscle cell suspension, the suspension was centrifuged for 5 min at 4000 rpm, the supernatant removed and replaced with 500 ul of DMEM containing 10% heat inactivated horse serum. The pellet was resuspended, and the tube centrifuged for a further 60 seconds at 2600 rpm, the supernatant was then removed and filtered through 40 micron nylon mesh (sterile disposable, Falcon brand). A sample of the cell suspension was inspected by microscopy at this stage to ensure correct cell morphology and sufficient cell density for flow cytometry (sub optimal densities were corrected by dilution, or by pelleting and resuspension).

For the liver cell suspension, the suspension was filtered through 40-micron nylon mesh, transferred to a clean microcentrifuge tube and pelleted as for muscle. The top layer of the pellet was carefully removed to a clean tube with complete DMEM (500 ul), taking care not to disturb the red blood cells which form a distinct and visible layer at the bottom of the pellet. The cell suspension was inspected at this stage and the cell density adjusted. If red blood cells were present in the cell preparation they were removed with a lysis step (incubating the cells in 1 ml lysis buffer containing 130 mM Ammonium Chloride, 17 mM Tris, 10 mM Sodium Bicarbonate for 5 minutes at room temperature).

For the brain cell suspension, the suspension was filtered and pelleted as described above. The pellet was resuspended in 250 ul complete Liebowitz (L-15) medium containing 10% horse serum and 6 g/l glucose, Percoll was added to produce a 50% solution (approx. 260–280 ul). The suspension was centrifuged at 3.5 k for 5 minutes, following which the top layer of cells was carefully removed into a clean microcentrifuge tube and diluted with at least 1 ml of L-15 medium. The cells were pelleted by centrifuging at 4000 rpm for 5 minutes and then were resuspended in an appropriate volume of L-15.

Figure 21:
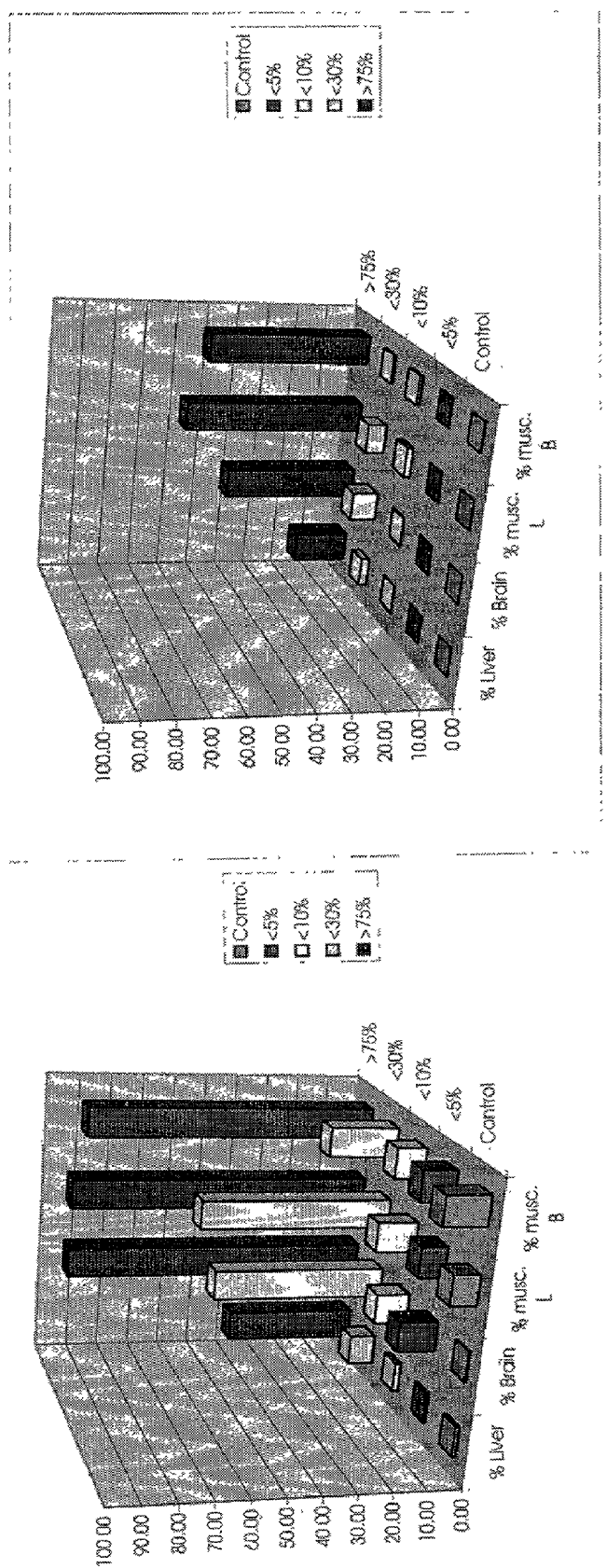
FIG. 21 is a summary of FACS data from chimeras made with non-transfected cells (control), chimeras made with ES cells that were transfected with CX/GFP/Puro and estimated to contain <5% donor-derived cells by feather pigmentation, chimeras made with ES cells that were transfected with CX/GFP/Puro and estimated to contain >5% and <10% donor-derived cells by feather pigmentation, chimeras made with ES cells that were transfected with CX/GFP/Puro and estimated to contain >10% and <30% donor-derived cells by feather pigmentation, chimeras made with ES cells that were transfected with CX/GFP/Puro and estimated to contain >30 and <75% donor-derived cells by feather pigmentation, and chimeras made with ES cells that were transfected with CX/GFP/Puro and estimated to contain >75% donor-derived cells by feather pigmentation. Cells were prepared as described in the text from liver, brain, and muscle. The mean number of fluorescent cells detected above the autofluorescent threshold is shown in the left panel; the mean number of fluorescent cells detected above the M2 threshold, which is an order of magnitude higher than the autofluorescent threshold is shown in the right panel.
Figure 22:
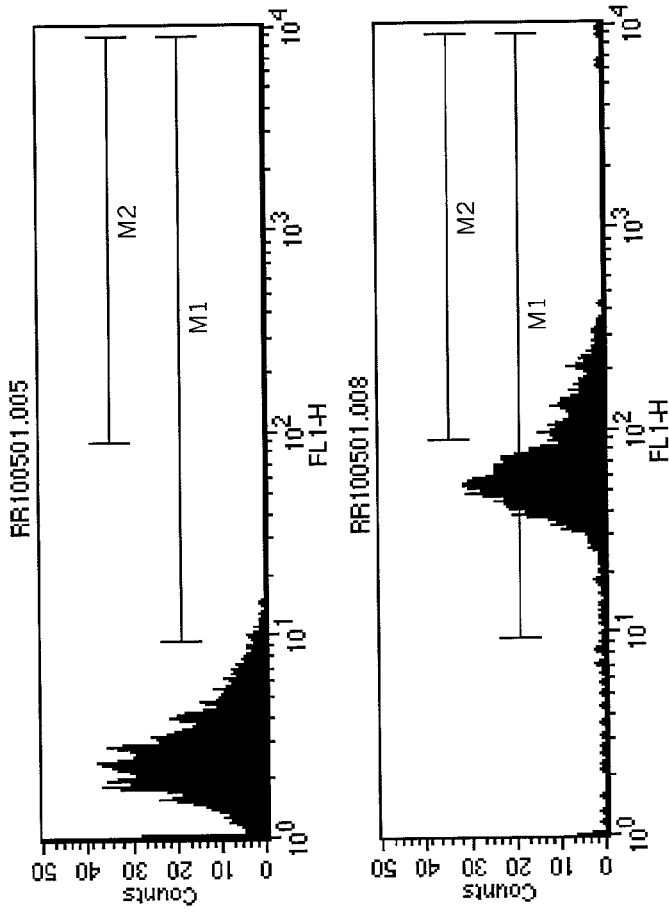
FIG. 22 is an example of a FACS analysis of cells prepared from the brain of a chimera made with non-transfected ES cells (upper panel) and chimeras that were made with cells transfected with CX/GFP/Puro (lower panel). Substantially all of the cells from the chimera made with transfected cells display a level of fluorescence that is above that of the cells from the control bird indicating that the contribution of the donor ES cells to the brain tissue of the chimera is extensive.
Figure 23:
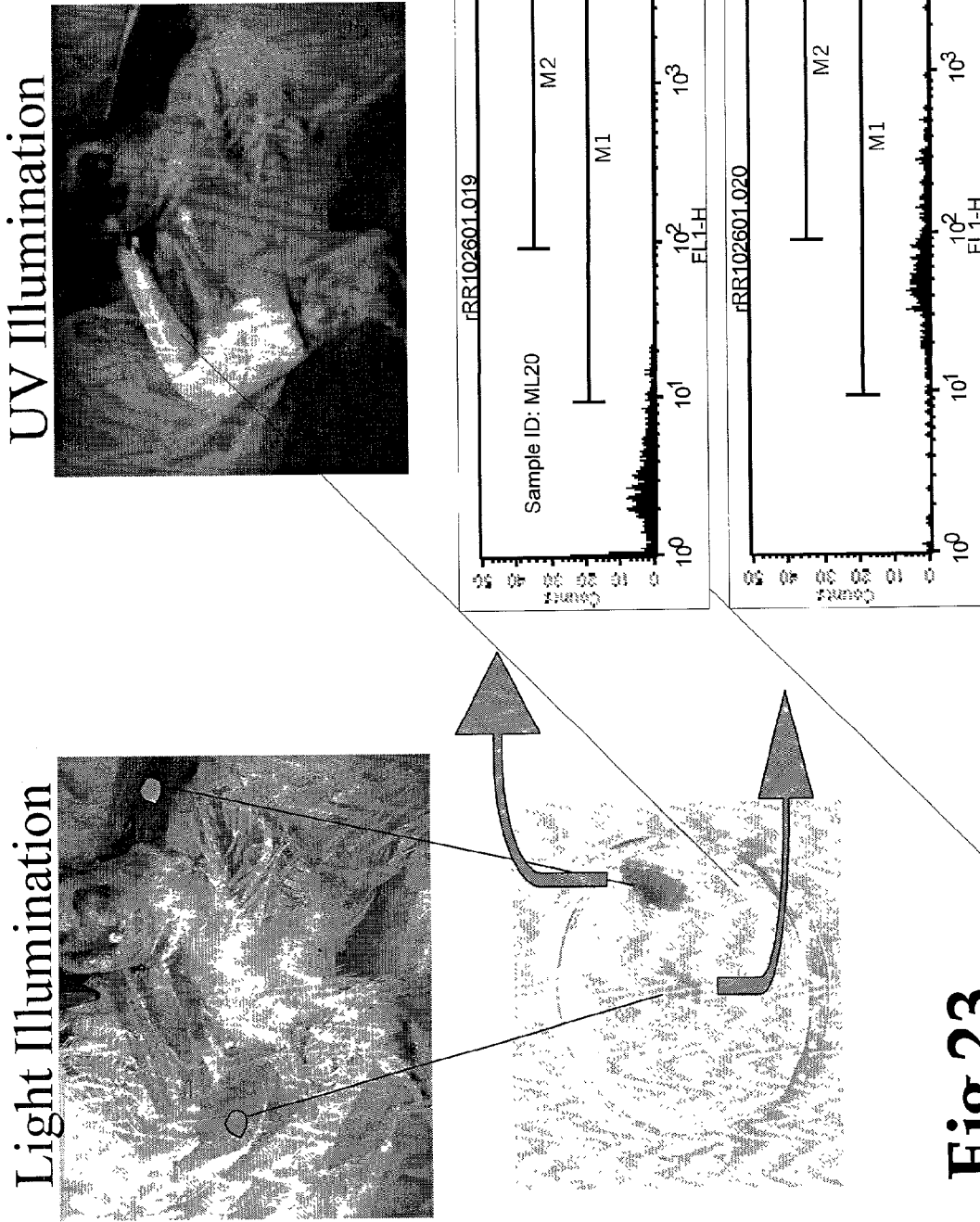
FIG. 23 is an example of a FACS analysis of cells prepared from leg muscles of a chimera that was made with cells transfected with CX/GFP/Puro. The right leg of this chimera was green to the naked eye indicating substantial contribution to this tissue. A preparation of cells from the fluorescent leg muscle was shown to contain primarily fluorescing cells by FACS analysis (lower panel). The left leg of the chimera was normal in color and a preparation of these cells was shown to contain non-fluorescing cells by FACS analysis. These data show that chimerism in tissues within the same animal may receive different contributions from donor ES cells.

A flow cytometric analysis of GFP expression was conducted in liver, brain and muscle cells from chimeras. Single cell suspensions were transferred into polystyrene tubes and loaded into a flow cytometer, for which the operating parameters had been set to detect the particular cell type of the sample, and which was equipped to detect emitted light at a green wavelength in response to an excitory laser beam. At each analysis, at least one group of samples from a non-transgenic chimera was analyzed in order to set the baseline for fluorescence measurement (since the flow cytometer detects some autofluorescence from each cell). These are referred to as control samples in FIG. 21. The data produced by the flow cytometer included the number of cells detected (within the parameters specified) and summarized the fluorescence of the cells in that population. Examples of the data from analyses of brain and muscle tissue is shown in FIGS. 22 and 23, respectively. Data was collected for the number of cells which exhibited a fluorescence intensity greater than the autofluorescent level set by the non-transgenic sample for each tissue type (designated M1). A susbset of these data was collected for cells which exhibited a fluorescence intensity at least ten times greater than the autofluorescent level (designated M2).

Brain, liver and muscle (breast and leg) samples were removed from twenty six chickens, of which 18 were chimeras that had been produced by injecting transgenic chicken ES cells carrying the GFP transgene into non-transgenic White Leghorn recipient embryos, as described above. The remaining 8 chickens were chimeras that were produced by injecting non-transfected cES cells into non-transgenic White Leghorn recipient embryos. Male and female chickens were present in both the groups. Green fluorescence was detected in brain-derived, liver-derived and muscle-derived cells from the transgenic chimeras. The fluorescence intensity and the ratio of fluorescent to non-fluorescent cells varied between birds and between tissue type. The tabulated results are shown in FIG. 21. In birds which had been awarded a low score for donor-derived feather pigmentation, or for green skin when screened with a UV lamp prior to post-mortem analysis, the number of fluorescent cells in the tissue samples was generally low or zero. Birds which scored well for these criteria (e.g. greater than 75% donor-derived feathers) were found to have fluorescent cells in all three tissue sample types, and this was the only group in which highly fluorescent (M2) cells were present in all three tissue types. Of the three tissue types, the number of fluorescent cells derived from the liver was the lowest. Brain and muscle-derived fluorescent cells were present in greater numbers and in a greater number of samples derived from the transgenic chimeras. The data is shown graphically in FIG. 19.

The data shows that transgenic cES cells, when injected into recipient stage X embryos, can thrive in the host and differentiate into liver, muscle and brain cells. Liver, muscle and brain are tissues that are derived from endoderm, mesoderm and ectoderm, respectively; thus cES cells may differentiate into the three major somatic cell lineages, from which all other somatic cells are derived. Further, this experiment shows that transgenic cES-derived cells persist beyond the embryonic stages and can be seen in juvenile chickens, and that the transgene continues to express in these diverse cell types.

The transgene is also present in lymphocytes derived from ES cells. The hemopeotic lineage, which comprises the lymphoid and myeloid lineages, is of particular interest in transgenic chimeras derived from ES cells because B cells in the lymphoid lineage produce antibodies. Lymphocytes are prepared either from blood samples taken from chimeric chickens at any time from hatching to adulthood or from the bursa of Fabricius of chimeric embryos. Bursae are removed from chicks at day 20 of embryonic development (E20) and macerated by forcing through steel mesh in 10 ml of Hanks' Buffered Salt Solution (HBSS) with the plunger of a 20 ml syringe. The resulting tissue fragments and cells are collected into a tube and incubated at room temperature for 5 minutes to allow the large fragments to settle. The cell supernatant is harvested and the cells are counted and then collected by centrifugation at 1500 g for 10 minutes at 4° C. and resuspended at a maximum of $1 \times 10^8$ cells per ml of HBSS in a 15 ml conical tube. Blood is collected (0.5 ml) from chimeric chickens' wing veins using a heparinized syringe and deposited into a vacuum tube containing EDTA to prevent clotting. Blood samples are mixed 1:1 with HBSS to give a final volume of 1 ml in a 15 ml conical tube. From this point on blood samples and bursa samples are treated the same way. One ml of cell suspension is underlayed with 0.75 ml Fico/Lite-LM (Atlanta Biologicals catalog number 1406) by dispensing the Fico/Lite at the bottom of the tube, underneath the cell suspension. The tubes are then centrifuged at 1500 g for 15 minutes at 4° C., no brake. The interface between the Fico/Lite and the HBSS is carefully harvested to collect the mononuclear cells that have concentrated there in a discrete layer of material. This material is transferred to a new tube triturated to break up the compacted cells and then mixed with 3 ml of HBSS/2% heat inactivated fetal bovine serum. The cells are collected by centrifugation at 1500 rpm in a Sorvall benchtop centrifuge, 10 minutes at 4° C., then washed two more times in HBSS/2% FBS. A small aliquot (25 µl) is mounted on a microscope slide for preliminary assessment of the extent of donor-derived GFP fluorescence under the microscope. The remainder of the cells are then ready for antibody staining or fixation.

To store cells for longer than a few hours before analysis or if they are to be permanently mounted on slides for microscopy, they are first fixed in paraformaldehyde. An aliquot of cells (50 µl, 0.5–1×10$^6$ cells) is fixed by adding 1 ml 4% paraformaldehyde and incubating at room temperature for 15 minutes. The cells are then washed three times by centrifugation at 500 g for 6 minutes in a microfuge to collect the cells, followed by resuspending the cells in PBS/2% heat inactivated fetal bovine serum.

In antibody staining, an aliquot of 0.5 ×10$^6$ cells in fresh PBS/2% FBS/0.1% sodium azide is placed in a tube or a well of a 96-well plate, on ice. Monoclonal antibodies conjugated to R-phycoerythrin (Southern Biotechnology Associates) are added to the cells and incubated for 30 minutes on ice, covered to protect the fluorophore. Antibodies that recognize the chicken B lymphocyte marker Bu-1 (used at a working dilution of 0.2 g/10$^6$ cells) or the chicken T cell marker CD3 (used at 0.5 g/10$^6$ cells) are used. After incubation the cells are washed three times by centrifugation at 500 g for 6 minutes, resuspending in 0.5 ml PBS/2% FBS/0.1% azide each time. After the final wash the cells are stored in 0.5% paraformaldehyde up to one week before analysis by flow cytometry. The paraformaldehyde is replaced with PBS/2% FBS on the day the cells are to be analyzed by flow cytometry; buffers without phenol red are used for flow cytometry. FACS analysis is performed for both GFP fluorescence and R-phycoerythrin fluorescence simultaneously, to detect the total proportion of cells that are donor derived (GFP-positive), the proportion of cells (both donor and recipient derived) that are stained by the antibodies (R-phycoerythrin-positive), and the proportion of donor derived cells that are also stained with the antibodies (GFP, R-phycoerythrin double positive).

Chimeras made with three different ES cell lines were analyzed for donor contribution to the lymphoid lineage, representing three different insertion sites for the CX-GFP marker (Table 9). A total of 27 chimeras have been analyzed, ranging in age from pre-hatch to adult. The proportion of donor-derived GFP-positive cells in the lymphocyte fraction ranged from 0 to 10% as judged by FACS analysis (animals with 0% are not shown in the table). Antibody staining of peripheral blood lymphocytes resulted in 5–17% of the cells staining with anti-Bu-1 antibodies and 75–85% of the cells staining with anti-CD3 antibodies. Staining of bursal lymphocytes with anti-Bu-1 antibodies resulted in over 90% of the cells stained. Double positive cells with GFP fluorescence and staining for either Bu-1 or CD3 and GFP were observed at low frequencies in several of the samples.

These data show that ES cells containing a gene encoding an exogenous protein contributed to the hemopoietic lineage in hatched chicks and mature animals.

TABLE 9

Contribution of cES cells to the lymphocyte lineage in somatic chimeras.

| Chimera | Age | GFP | Bu-1+ | CD3+ | GFP+ and Bu-1+ | GFP+ and CD3+ | Sex | Feather | Green Score | Cell line |
|---|---|---|---|---|---|---|---|---|---|---|
| OV-36 | 10 | 10 | ND | ND | ND | ND | F | 15 | ND | OVF |
| OV-21 | 10 | 7 | 5 | 85 | 0 | 0 | M | 0 | ND | OVF |
| 10881 | 67 | 5 | 17 | 75 | 0.03 | 1 | M | 60 | 3 | TB01 |
| 10891 | 49 | 3 | 12 | 74 | 0 | 0.1 | F | 5 | 1 | TB01 |
| 10821 | 111 | 1 | ND | ND | ND | ND | M | 75 | 3 | TB01 |
| 10877 | 98 | 1 | 11 | ND | 0.04 | ND | F | 75 | 4 | TB01 |
| IG1-25 | E20 | 0.2 | 95 | ND | 0.03 | ND | F | 70 | ND | BAC A |
| 10845 | 146 | 0.18 | 8.5 | ND | 0 | ND | M | 60 | 3 | TB01 |

The eight chimeras listed in the table were found to contain cES cell-derived lymphocytes. Peripheral blood lymphocytes (or bursal lymphocytes in the case of chimera IG1-25) were prepared with Fico/Lite-LM as described in the text. Lymphocytes were then analyzed for expression of green fluorescent protein (GFP), the Bu-1 B cell associated alloantigen (Bu-1), and the CD3 member of the T cell receptor-associated CD3 complex (CD3). The numbers in the columns labeled with GFP, Bu-1 and CD3 indicate the percentage of cells in each sample that positive for those markers by FACS analysis (except for OV-36 and 10821 in which the percentage of GFP fluorescing cells was determined by counting cells under the microscope). The age of the chimeras when samples were taken for analysis is indicated in days, and the sex of each chimera is indicated. The column labeled "Feather" indicates the percentage estimate of black, cES cell derived feather pigmentation, with 75 being the highest amount of black possible (as pure Barred Rock chickens themselves have a plumage that is approximately 75% black). "Green score" is a subjective evaluation of overall green fluorescence in the whole animal visualized by shining a handheld UV lamp on the live animal. The scale is from 0 (no green) to 4 (the most green). This score is used as a further indication of the overall extent of cES cell contribution in each animal. "Cell line" indicates the names of the different cES cell lines used to generate the chimeras.

There will be various modifications, improvements, and applications of the disclosed invention that will be apparent to those of skill in the art, and the present application encompasses such embodiments to the extent allowed by law. Although the present invention has been described in the context of certain preferred embodiments, the full scope of the invention is not so limited, but is in accord with the scope of the following claims. All references, patents, or other publications are specifically incorporated by reference herein.

We claim:

1. A method of creating a chimeric chicken comprising:
   selecting chicken embryonic stem cells having a genome comprising a stably integrated transgene from a culture sustained for more than 60 days,
   injecting the embryonic stem cells into a recipient chicken embryo, and
   hatching a chimeric chicken from the recipient chicken embryo injected with said embryonic stem cells wherein expression of the stably integrated transgene is detected in at least one tissue type of the chimeric chicken.

2. The method of claim 1 wherein the injecting step is comprised of injecting embryonic stem cells into a compromised embryo.

3. The method of claim 2 wherein the embryo is compromised by gamma irradiation.

4. The method of claim 2 wherein the embryo is compromised by mechanical removal of cells from the embryo.

5. The method of claim 1 wherein the expression of the stably integrated transgene is detected in extra-embryonic tissue.

6. The method of claim 1 wherein the expression of the stably integrated transgene is detected in somatic tissue.

7. The method of claim 6 wherein the somatic tissue is ectodermal.

8. The method of claim 6 wherein the tissue is endodermal.

9. The method of claim 6 wherein the tissue is mesodermal.

* * * * *